(12) United States Patent
Swanson et al.

(10) Patent No.: US 8,096,990 B2
(45) Date of Patent: Jan. 17, 2012

(54) ABLATIVE TREATMENT OF THE HEART TO IMPROVE PATIENT OUTCOMES FOLLOWING SURGERY

(75) Inventors: David K. Swanson, Campbell, CA (US); Arthur A. Bertolero, Danville, CA (US)

(73) Assignee: Endoscopic Technologies, Inc., San Ramon, CA (US)

( * ) Notice: Subject to any disclaimer, the term of this patent is extended or adjusted under 35 U.S.C. 154(b) by 1318 days.

(21) Appl. No.: 11/651,439

(22) Filed: Jan. 8, 2007

(65) Prior Publication Data

US 2007/0156185 A1 Jul. 5, 2007

Related U.S. Application Data

(63) Continuation-in-part of application No. 11/186,148, filed on Jul. 20, 2005, now Pat. No. 7,591,818, which is a continuation-in-part of application No. 10/988,021, filed on Nov. 12, 2004, now Pat. No. 7,399,300, which is a continuation-in-part of application No. 10/410,618, filed on Apr. 8, 2003, now Pat. No. 7,226,448, which is a continuation-in-part of application No. 10/272,446, filed on Oct. 15, 2002, now Pat. No. 6,849,075.

(60) Provisional application No. 60/519,726, filed on Nov. 12, 2003, provisional application No. 60/337,070, filed on Dec. 4, 2001.

(51) Int. Cl.
*A61B 18/04* (2006.01)
*A61B 18/18* (2006.01)

(52) U.S. Cl. ......................... 606/45; 606/49
(58) Field of Classification Search ............ 606/41, 606/45–50; 607/115, 116, 122
See application file for complete search history.

(56) References Cited

U.S. PATENT DOCUMENTS

| | | | |
|---|---|---|---|
| 5,938,694 A * | 8/1999 | Jaraczewski et al. | 607/122 |
| 6,039,733 A | 3/2000 | Buysse et al. | |
| 6,110,106 A | 8/2000 | MacKinnon et al. | |
| 6,237,605 B1 | 5/2001 | Vaska et al. | |
| 6,292,695 B1 * | 9/2001 | Webster et al. | 607/14 |
| 6,514,250 B1 | 2/2003 | Jahns et al. | |
| 6,652,518 B2 | 11/2003 | Wellman et al. | |

(Continued)

OTHER PUBLICATIONS

Chiou, CW et al., "Efferent vagal innervation of the canine atria and sinus atriventricular nodes. The third fat pad.", Circulation 1997; 95: 2573-2584.

(Continued)

*Primary Examiner* — Roy Gibson
(74) *Attorney, Agent, or Firm* — James J. Leary; GSS Law Group

(57) ABSTRACT

Devices and methods are described for ablation of cardiac tissue for treating cardiac arrhythmias, such as atrial fibrillation. Devices may include a tissue contacting member for contacting epicardial tissue and securing the ablation device to the epicardial tissue and an ablation member for ablating the tissue. Suction apertures attach the contacting member to the epicardial surface with sufficient strength to stabilize the tissue with the device. The devices and methods can be used to ablate epicardial tissue in the vicinity of a pulmonary vein or to ablate cardiac tissues in other locations on a heart. A combined pacing and ablation probe is described for treating cardiac arrhythmia by: advancing the probe through an incision into the vicinity of the patient's heart, verifying at least one location of a cardiac parasympathetic ganglion, and applying ablation energy to the cardiac parasympathetic ganglion.

28 Claims, 16 Drawing Sheets

U.S. PATENT DOCUMENTS

| | | | |
|---|---|---|---|
| 6,692,491 | B1 | 2/2004 | Phan |
| 6,761,716 | B2 | 7/2004 | Kadhiresan et al. |
| 6,780,181 | B2 | 8/2004 | Kroll et al. |
| 7,686,803 | B2 * | 3/2010 | Mohan et al. .................... 606/41 |
| 7,769,441 | B2 * | 8/2010 | Foreman et al. ................. 607/2 |
| 7,828,795 | B2 * | 11/2010 | Privitera et al. ................ 606/41 |
| 2003/0158548 | A1 | 8/2003 | Phan et al. |
| 2004/0073206 | A1 * | 4/2004 | Foley et al. .................... 606/34 |
| 2005/0033137 | A1 * | 2/2005 | Oral et al. ..................... 600/374 |
| 2006/0287648 | A1 * | 12/2006 | Schwartz ....................... 606/27 |

OTHER PUBLICATIONS

Balser, Jeffrey R. et al., "Managing Arrhythmias in Patients After Cardiac Surgery: Improving the Standard of Care", Feb. 2000, 3 pages.

Pausjenssen, L.E. et al, "Atrial Fibrillation Following Coronary Artery Bypass Grafting", CACRC, Sep. 2002.

Raman, J. et al., "Surgical radiofrequency ablation of both atria for atrial fibrillation: Results of a multicenter trial", J. Thoracic and Cardiovascular Surgery, Nov. 2003, vol. 126, No. 5, 1357-1366.

Alex, J. et al., "Evaluation of Ventral Cardiac Denervation As a Prophylaxis Against Atrial Fibrillation After Coronary Artery Bypass Grafting", Soc. Thoracic Surgeons, 2005; 79: 517-20.

Pachon, J.C. et al., "Cardioneuroablation—new treatment for neurocardiogenic syncope, functional AV block and sinus dysfunction using catheter RF-ablation", Eurospace 2005 7(1):1-13.

Berrie, Chris, Predictors for Atrial Fibrillation and Thirty-Day Mortality in Patients Undergoing Aortic Valve Replacement for Isolated Aortic Stenosis: Presented at ESC, Sep. 12, 2005, 3 pages.

* cited by examiner

ABLATIVE TREATMENT OF THE HEART TO IMPROVE PATIENT OUTCOMES FOLLOWING SURGERY

CROSS REFERENCE TO OTHER APPLICATIONS

This application is a continuation-in-part of U.S. patent application Ser. No. 11/186,148 filed Jul. 20, 2005 now U.S. Pat. No. 7,591,818, which is a continuation-in-part of U.S. patent application Ser. No. 10/988,021 filed Nov. 12, 2004 now U.S. Pat. No. 7,399,300, which is a continuation-in-part application of U.S. patent application Ser. No. 10/410,618, which was filed on Apr. 8, 2003 now U.S. Pat. No. 7,226,448, which is a continuation-in-part of U.S. patent application Ser. No. 10/272,446, which was filed Oct. 15, 2002, now U.S. Pat. No. 6,849,075, which claims priority to U.S. Provisional Patent Application Ser. No. 60/337,070, filed Dec. 4, 2001. application Ser. No. 10/988,021 also claimed the benefit of U.S. Provisional Patent Application Ser. No. 60/519,726, filed Nov. 12, 2003. The entire contents of these applications are hereby incorporated by reference in their entirety.

BACKGROUND OF THE INVENTION

The present invention relates generally to medical devices and methods. More specifically, the invention relates to devices and methods for ablating epicardial and pericardial tissue to treat cardiac arrhythmias such as atrial fibrillation. The methods can be applied in combination with a cardiac or thoracic surgical procedure to treat atrial fibrillation prophylactically in patients determined to be at high risk for developing atrial fibrillation as a sequella to the surgery.

Atrial fibrillation (AF) is a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3% of those aged 50-59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be under-prescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Another area that has been identified as a location for arrhythmia-triggering foci is in the parasympathetic nerves that innervate the cardiac tissue as part of the autonomic nervous system. The normal function of the cardiac parasympathetic nerves is to slow down the heart rate in a relaxation response. However, fibrillated signals originating from the parasympathetic nerves can result in AF. The three main ganglia of the cardiac parasympathetic nerves are located in para-cardiac fat pads, the locations of which are shown in FIGS. 11A and 11B.

1. Ganglion A, located between the superior vena cava and the aortic root just above the right superior pulmonary vein;
2. Ganglion B, located between the right superior pulmonary vein and the right atrium; and
3. Ganglion C, located between the inferior vena cava and the right/left atrium.

Ganglion B gives most of the cardiac parasympathetic innervation. Ganglion C gives origin to the main part of the AV nodal innervation. Most of the vagal efferent cardiac fibres pass through ganglion A and thence to ganglia B and C. Only a few efferent fibres directly enter the B and C ganglia.

Therefore, it is feasible to achieve parasympathetic denervation by ablating ganglion B and AV nodal denervation by ablating ganglion C. However, ablation of ganglion A provides additional and significant sinus and AV node denervation. (Jose C. Pachon M, Enrique I. Pachon M, Juan C. Pachon M, Tasso J. Lobo, Maria Z. Pachon, Remy N. A. Vargas and Adib D. Jatene "Cardioneuroablation"—new treatment for neurocardiogenic syncope, functional AV block and sinus dysfunction using catheter RF-ablation Europace 2005 7(1): 1-13; doi:10.1016/j.eupc.2004.10.003; Chiou C W, Eble J N, Zipes D P. Efferent vagal innervation of the canine atria and sinus and atrioventricular nodes. The third fat pad. Circulation 1997; 95: 2573-2584.)

Post operative AF is a significant problem for hospitals worldwide with no effective solution. AF is the most common morbidity event after coronary bypass grafting. It has been estimated that the incidence of AF following coronary artery bypass graft (CABG) surgery is between 25% and 40%. The rate is even higher for patients undergoing valve surgery either alone or in combination with CABG surgery. Although the AF may resolve itself within the first ten days following surgery, the problem is associated with high levels of morbidity during the post operative phase and can increase the cost of hospital stays by $20,000 or more.

Other patients at high risk for developing AF include patients with ventricular fibrillation, patients undergoing pulmonary lobectomy surgery, and patients with mitral valve disease or heart failure and patients over 70 years of age.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. For example, certain antiarrhythmic drugs, like quinidine and procainamide, can reduce both the incidence and the duration of atrial fibrillation episodes. Yet, these drugs often fail to maintain sinus rhythm in the patient. Cardioactive drugs, like digitalis, Beta blockers, and calcium channel blockers, can also be given to control the ventricular response. However, many people are intolerant to such drugs. Anticoagulant therapy also combats thromboembolic complications, but does not eliminate them. Unfortunately, pharmacological remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

Maze-like procedures have also been developed utilizing catheters which can form lesions on the endocardium to effectively create a maze for electrical conduction in a predetermined path. Exemplary catheters are disclosed in commonly assigned U.S. Pat. No. 5,582,609. Typically, the lesions are formed by ablating tissue with an electrode carried by the catheter. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Although cardiac ablation devices and methods are currently available, many advances may still be made to provide improved devices and methods for ablating-epicardial tissue to treat AF and other arrhythmias. For example, currently available devices can be difficult to position and secure on epicardial tissue to perform an ablation. Devices such as bipolar ablation clamps and others can ablate tissue only in very limited patterns, such as one or two straight lines. Ablation devices often have no means for shielding ablative energy, to avoid unwanted burning of tissues in the vicinity of the heart, such as the esophagus. Relatively few devices can be secured to epicardial tissue with sufficient force to allow for stabilization of the heart. And many ablation devices may not be introduced by minimally invasive means, thus requiring an open surgical procedure. Typically, therefore, current cardiac ablation procedures for AF treatment still require stopping the heart and using a cardiopulmonary bypass apparatus.

Therefore, a need exists for improved devices and methods for ablating epicardial tissue to prophylactically treat AF and other cardiac arrhythmias to improve patient outcomes following surgery. Preferably, such devices and methods would provide ablation adjacent to and/or encircling one or more pulmonary veins, to disrupt conduction pathways and thus partially or completely treat AF. Also preferably, such devices and methods would allow for minimally invasive ablation procedures, in some cases on a beating heart. Such devices might also provide additional advantages, such as advantageous ablation patterns, shielding of ablative energy and/or the like. At least some of these objectives will be met by the present invention.

BRIEF SUMMARY OF THE INVENTION

Devices and methods of the present invention provide for ablation of cardiac tissue for treating cardiac arrhythmias such as atrial fibrillation. Although the devices and methods are often used to ablate epicardial tissue in the vicinity of at least one pulmonary vein, various embodiments may be used to ablate other cardiac tissues in other locations on a heart. Generally, devices of the invention include a tissue contacting member for contacting a portion of the epicardial tissue of a heart and securing the ablation device to the epicardial tissue, and an ablation member for ablating at least a portion of the tissue. In various embodiments, the devices have features which enable the device to attach to the epicardial surface with sufficient strength to allow the tissue to be stabilized via the device. For example, some embodiments may be used to stabilize a beating heart to enable a beating heart ablation procedure. Many of the devices may be introduced into a patient via minimally invasive incisions, introducer devices and the like. Although much of the following description focuses on using devices and methods of the invention to treat atrial fibrillation (AF) by ablating epicardial tissue on a human heart, the devices and methods may be used in veterinary or research contexts, to treat various heart conditions other than atrial fibrillation and/or to ablate cardiac tissue other than the epicardium.

In one aspect, a system for treating heart tissue to treat a cardiac arrhythmia comprises: at least one energy transmission member for applying energy to the heart tissue in a pattern to treat the cardiac arrhythmia; at least one tissue securing member coupled with the at least one energy transmission member for enhancing contact of the energy transmission member with the heart tissue; and at least one guiding member coupled with at least one of the energy transmission member and the tissue securing member for guiding the energy transmission member and the tissue securing member to a location for treating the heart tissue.

Optionally, such as system may further include at least one visualization member for enhancing visualization of the heart tissue and the treatment location. In some embodiments, for example, the visualization member may include an optic imaging device, a thermal imaging device, an ultrasound device, an electrical imaging device, a Doppler imaging device or the like, though any suitable device may be used. In some embodiments, an optic imaging device comprises a fiber optic device positionable to view a posterior portion of the heart tissue. In other embodiments, a thermal imaging device measures at least one heat transfer coefficient of the heart tissue to determine at least one of a type and a thickness of the heart tissue. In still other embodiments, an electrical imaging device measures electrical resistance and/or impedance of the heart tissue to determine a type and/or a thickness of the heart tissue.

In some embodiments, the at least one visualization member is removably coupled with at least one of the at least one energy transmission member, the at least one tissue securing member and the at least one guiding member. Also in some embodiments, the at least one visualization member may comprise at least one optic member for acquiring optic signals of an area to be visualized, and wherein the visualization member includes at least one inflatable member coupled with the visualization member at or near the optic member. For example, the inflatable member may provide a space in a body cavity and/or between at least two body tissues to enhance operation of the optic member. In some embodiments, the inflatable member includes an inflation port in fluid communication with an inflation lumen coupled with the visualization member for allowing introduction of a liquid or a gas to inflate the inflatable member. In some embodiments, the inflatable member reduces motion of the heart tissue when applied to the heart tissue.

Some embodiments of the invention also include at least one positioning device for contacting the heart tissue and positioning the heart tissue for treatment. For example, the positioning device may comprise a suction positioning device. In some embodiments, the positioning device reduces motion of a beating heart to further position the heart tissue for treatment.

The energy applied to the heart tissue may be any suitable energy, such as but not limited to radio frequency energy, ultrasound energy, microwave energy, cryogenic energy, thermoelectric energy and laser energy. In some embodiments, optionally, the energy transmission member contacts an epicardial surface of the heart tissue to transmit the energy, and wherein the energy is transmitted from the epicardial surface through the heart tissue to an endocardial surface. Sometimes, the energy is further transmitted through at least one of fat and connective tissue covering at least part of the epicardial surface. Some embodiments also include at least one grounding device for dispersing the energy from a patient undergoing an energy transmission heart procedure. Some embodiments may also include at least one needle coupled with the energy transmission member for insertion into the heart tissue to enhance the application of energy to the heart tissue. In some of these embodiments, the energy is transmitted from a tip of each needle. Optionally, the needle may be retractable. In some embodiments, for example, the retractable needle is exposed and retracted via a pneumatic member coupled with the energy transmission member. In some embodiments, the retractable needle is exposed and retracted automatically when the energy transmission member contacts the heart tissue. Also in some embodiments, the depth of penetration of the retractable needle into the heart tissue is adjustable.

Some embodiments may also include at least one closed circuit feedback loop for measuring and regulating operation of the energy transmission member. In some embodiments, either the energy transmission member or the tissue securing member further comprises at least one fluid aperture for applying fluid to the heart tissue to enhance the application of energy to the heart tissue.

In some embodiments, the energy transmission member is coupled with at least one guiding member such that a change in shape of the guiding member causes a corresponding change in shape of the energy transmission member. For example, the guiding member may comprise a deformable linear member its shape being adjustable by a user, and wherein the energy transmission member comprises a deformable linear member coaxially coupled with the guiding member so as to move with the guiding member. In some embodiments, the guiding member is adjustable to at least partially encircle at least one pulmonary vein.

In some embodiments, the tissue securing member includes at least one connector for removably coupling with the at least one energy transmission member. Sometimes, the tissue securing member is conformable to a surface topography of the heart tissue. In various embodiments, a first longitudinal axis of the tissue securing member and a second longitudinal axis of the removably coupled energy transmission member may be collinear, parallel to one another or offset from one another. In some embodiments, the energy transmission member comprises a linear member, and the connector comprises a plurality of connectors disposed along a length of the tissue securing member for removably coupling the linear member with the tissue securing member. The tissue securing member may allow compressive force to be applied between the at least one energy transmission member and the heart tissue.

In some embodiments, the tissue securing member comprises at least one vacuum applying member. The vacuum applying member may comprise, for example: at least one vacuum lumen; at least one vacuum port in fluid communication with the lumen for coupling the lumen with a vacuum source; and at least one aperture in fluid communication with the lumen for applying vacuum force to the heart tissue. In some embodiments, the vacuum lumen comprises multiple, separate lumens, and each separate lumen is in fluid communication with a separate vacuum port. Such embodiments may optionally further include means for selectively applying vacuum to one or more of the separate lumens without applying vacuum to one or more other separate lumens.

In other embodiments, the tissue securing member comprises at least one expansible balloon member. The expansible balloon member may include at least one fluid introduction port for allowing introduction of a liquid or a gas to expand the balloon member. Some embodiments include multiple, separate balloon members, wherein each separate balloon member is in fluid communication with a separate fluid introduction port. Such embodiments may also include means for selectively introducing fluid into one or more of the separate balloons without introducing fluid into one or more other separate balloons. Optionally, in some embodiments, the tissue securing member prevents a portion of the heart tissue from being treated by the at least one energy transmission member. For example, the tissue securing member may comprise at least one insulation material for preventing the portion of the heart tissue from being treated. In one embodiment, the insulation material further prevents the at least one energy transmission member from contacting or harming other, non-cardiac tissue of the patient and from contacting or harming a user of the energy transmission member.

In some embodiments, the guiding member comprises at least one of an elongate shaft, a steerable guidewire and an introducer sheath. For example, the steerable guidewire may comprise a pushable guidewire having at least one relatively stiff portion and one relatively flexible portion for positioning the energy transmission member in a location for treatment. For example, the steerable guidewire may comprise a pullable guidewire to which tension is applied to steer the guidewire to position the energy transmission member in a location for treatment.

In another aspect, a system for treating heart tissue to treat a cardiac arrhythmia comprises: at least one therapeutic agent transmission member for applying at least one therapeutic agent to the heart tissue in a pattern to treat the cardiac arrhythmia; at least one tissue securing member coupled with the at least one energy transmission member for enhancing contact of the energy transmission member with the heart tissue; and at least one guiding member coupled with at least one of the energy transmission member and the tissue securing member for guiding the energy transmission member and the tissue securing member to a location for treating the heart tissue. In some embodiments, for example, the therapeutic agent transmission member comprises at least one lumen and at least one aperture in the lumen for allowing passage of the at least one therapeutic agent out of the lumen to contact the heart tissue.

Optionally, such a system may further include at least one needle coupled with the therapeutic agent transmission member for insertion into the heart tissue to enhance application of the at least one therapeutic agent to the heart tissue. The therapeutic agent transmission member itself may comprise at least one needle and at least one aperture adjacent a tip of each needle for allowing passage of the at least one therapeutic agent out of the needle to contact the heart tissue. Optionally, the needle may be retractable. For example, the retractable needle may be exposed and retracted via a pneumatic member coupled with the therapeutic agent transmission member. In some embodiments, the retractable needle is exposed and retracted automatically when the therapeutic agent transmission member contacts the heart tissue. Also in some embodiments, a depth of penetration of the retractable needle into the heart tissue is adjustable.

In another aspect of the invention, a method for treating heart tissue of a patient to treat a cardiac arrhythmia involves: advancing at least one treatment member coupled with at least one tissue securing member through an incision on the patient; visualizing a treatment area in the patient with at least one visualization member; contacting the heart tissue of the patient with the treatment member and the tissue securing member; applying a force, through the tissue securing member, to enhance contact of the treatment member with the heart tissue; and treating the heart tissue, using the at least one treatment member. In some embodiments, the treatment member and/or the tissue securing member are advanced through a port applied to the patient, the port having a diameter no greater than 5 cm.

In some embodiments, the advancing step includes guiding the treatment member and/or the tissue securing member using at least one guiding member. Guiding may involve, for example, using a pushable guidewire having at least one relatively stiff portion and one relatively flexible portion for positioning the treatment member in a location for treatment. Alternatively, guiding may involve using a pullable guidewire to which tension is applied to steer the guidewire to position the treatment member in a location for treatment.

Some embodiments of the method further include using at least one positioning device to position the heart tissue for treatment. This may involve, for example, applying suction to the heart tissue. In some embodiments, using the positioning device reduces motion of the heart tissue. In other embodiments, contacting the heart tissue comprises applying a suction force with the tissue securing member to increase a contact surface area of the tissue securing member with the heart tissue. Applying the suction force may further comprise providing consistent contact force between the heart tissue and the tissue securing member. Optionally, applying the suction force may comprise securing the tissue securing member and the treatment member to the heart tissue, the tissue securing member and the treatment member having the same cross-sectional shape.

In some embodiments, treating the heart tissue comprises applying energy to the heart tissue in a pattern to reduce or eliminate the cardiac arrhythmia. The applied energy may be in any suitable form, such as radio frequency energy, ultrasound energy, microwave energy, cryogenic energy, thermoelectric energy or laser energy. In some embodiments, the energy is applied to an epicardial surface of the heart, wherein the energy is transmitted from the epicardial surface through the heart tissue to an endocardial surface. Optionally, the energy may be further transmitted through fat and/or connective tissue covering at least part of the epicardial surface. Some methods may further include dispersing the energy from the patient through at least one grounding device coupled with the patient.

Some embodiments further involve inserting at least one needle into the heart tissue to enhance the application of energy to the heart tissue. For example, the energy may transmitted from a tip of each needle. Some methods include extending the at least one needle from a retracted position before applying the energy and retracting the at least one needle to the retracted position when the energy has been applied. Such methods may also include selecting a depth of penetration of the at least one retractable needle into the heart tissue. Other embodiments may involve measuring the application of energy to the heart tissue using at least one closed circuit feedback loop and regulating the application of energy to the heart tissue based on the measurement. Still other embodiments may include applying fluid to the heart tissue to enhance the application of energy to the heart tissue.

In alternative embodiments, treating the heart tissue comprises applying at least one therapeutic agent to the heart tissue in a pattern to reduce or eliminate the cardiac arrhythmia. For example, applying the at least one therapeutic agent may involve infusing the agent through at least one aperture in the at least one treatment member. In some embodiments, the therapeutic agent is infused through at least one aperture in at least one needle coupled with the treatment member. In some embodiments, applying the at least one therapeutic agent comprises inserting at least one needle into the heart tissue to a desired depth, injecting the at least one agent into the heart tissue, and removing the at least one needle from the heart tissue. Such a method may further include extending the at least one needle from a retracted position for insertion into the heart tissue and retracting the at least one needle to the retracted position after injection.

Yet another embodiment may include adjusting a shape of a guiding member coupled with the at least one treatment member to alter the shape of the treatment member. In some embodiments, adjusting the shape of the guiding member allows the treatment member to conform to a surface of the heart tissue. Also in some embodiments, adjusting the shape of the guiding member allows the treatment member to at least partially encircle at least one pulmonary vein. Some embodiments may also include removably coupling the tissue securing member with the at least one treatment member. Some embodiments may further include conforming the tissue securing member to a surface topography of the heart tissue.

In some embodiments, applying force comprises applying compressive force between the at least one treatment member and the heart tissue. Applying the compressive force, in turn, may comprises applying vacuum force via at least one vacuum member of the tissue securing member. Such methods may further involve applying the vacuum force through at least a portion of the vacuum member while not applying the vacuum force through at least another portion of the vacuum member. In some embodiments, applying the compressive force comprises applying force via at least one expansible balloon member. A method may further comprising preventing, using the tissue securing member, a portion of the heart tissue from being treated by the at least one treatment member. For example, the tissue securing member may comprise at least one insulation material for preventing the portion of the heart tissue from being treated.

In some embodiments, visualizing comprises using at least one visualization member selected from the group consisting of an optic imaging device, a thermal imaging device, an ultrasound device, an electrical imaging device and a Doppler imaging device. Some embodiments also include expanding an expansible balloon coupled with the visualization member near an optic element to enhance visualization. Sometimes, expanding the balloon provides a space in a body cavity and/or between at least two body tissues to enhance operation of the optic member. Optionally, expanding the balloon may reduce motion of the heart tissue when applied to the heart tissue.

The invention also includes ablation systems which include an ablation energy source for providing energy to the ablation device. The ablation energy source of the invention is particularly suited for use with ablation apparatus as described herein using RF energy, but is not limited to such use, and other kinds of ablation energy sources and ablation devices may be useable in the invention. A typical RF ablation system comprises a RF generator which feeds current to an ablation device, including those described in this application, containing a conductive electrode for contacting targeted tissue. The electrical circuit is completed by a return path to the RF generator, provided through the patient and a large conductive plate, which is typically in contact with the patient's back.

In some embodiments, the ablation system is configured to recognize the kind of ablation device connected by including keyed plugs, which describes specialized socket shapes configured to accept only plugs which are manufactured with the matching shape. The energy source includes predetermined settings appropriate for the kind of device that is accepted by that socket. In another embodiment, the ablation system of the invention includes apparatus for recognizing the kind of device that has been coupled to the energy source and for automatically adjusting various settings to accommodate the detected device.

In further embodiments the ablation device may be inserted minimally invasively under stress, and is configured to conform to the topography or anatomy of the tissue to be treated when relaxed. This feature may enhance the adherence of the ablation device to the tissue because the suction is not working against resistance of the ablation device to conforming to the desired shape.

In other embodiments, the ablation device may include indicators for identifying which ablation element is to be activated. For example, the ablation device may include different colored lines to assist the user in distinguishing the orientation and alignment of the ablation device.

In some embodiments, the ablation device may be configured to allow the ablation member to extend beyond the edge of the tissue contacting member to allow for ablation to occur outside of the region covered by the tissue contacting member.

In another embodiments, the artery securing arms may instead be configured to grasp a second ablation member, thereby allowing ablation to occur outside of the region covered by the tissue contacting member.

In some embodiments the length of the suction pods may be varied such that suction pods of more than one length are used on the same tissue contact member. Furthermore, the suction pods may be spaced apart or placed in groupings separated by slected lengths. Some or all of the length of the ablation device used to emit ablation energy may not include any suction pods. In some embodiments an insulated member may cover the majority of the geometry of the ablation device such that only areas contacting target tissue can emit energy that will penetrate the tissue. This feature may protect surrounding tissues from unintentional ablation. Positioning the ablation member within an insulating tissue contacting member provides a safety margin protecting adjacent tissue that is not intended to be ablated. The insulated member may includes lumens for delivering saline to lower impedance or increase conductivity or other substance to improve performance and efficiency of energy emission.

The suction force may be used to create a fluid gradient through the thickness of the tissue. A dynamic fluid gradient may enhance energy conduction.

In some apparatus and methods of the invention, once the tissue contact member is positioned and suctioned onto the heart, the probe may also be slid within the probe channel in the tissue contact member so that the energy emitting section of the ablation member may be positioned as a separate step from the step of positioning the tissue contacting member. It is also possible to position the tissue contacting member separately from the ablation member, then in a later step, slide the ablation member into the tissue contact member. In some embodiments, an ablation member with a short energy emitting section may be moved along a channel in the tissue contact member so that the device can create long lesions, perhaps longer than the ablation section of the ablation member, with minimal manipulations of the device within the track.

Using a single placement of the tissue contacting member may enhance continuity of ablation lesions. Not having to move the ablation device between discrete ablation cycles, and instead only moving the ablation member within the tissue contacting member, insures that adjacent ablation segments are contiguous with no ablation gaps. Avoiding the creation of gaps can be critical to insure electrical isolation of desired tissue areas, and may also decrease procedure time by not requiring the surgeon to verify overlap of adjacent ablation lesions In some embodiments the preferred features of the material used to manufacture the tissue contacting member include one or more of the following: the material provides electrical or thermal insulation, the material is flexible to facilitate remote advancement via torturous pathways, the material has shape memory allowing large elastic deformation of the tissue contacting member but also allowing the tissue contacting member to return to a preformed shape in a relaxed configuration, the material may be translucent or transparent to help the user see the position of the ablation probe, and the material may be lubricious to facilitate insertion and placement.

The method may further include the steps of using visual and audible cues to verify the ablation device is adhered to tissue. For example the user can hear a suction sound or 'whistle' when the suction has been activated and the ablation device is not correctly adhered. Also, the user can hear vacuum pump elevate as vacuum increases. In some embodiments, the user can visually observe the tissue contacting member collapse when the ablation device is correctly adhered and suction is activated.

In some embodiments, the preferred vacuum pressure is −200 mmHG to −760 mmHG.

In still further embodiments, the ablation device may include more electrodes that are available on the energy source. In this embodiment, the ablation device includes a plurality of electrodes, and wherein the energy source includes less electrodes than the ablation device. Further, the ablation device includes at least two plugs, with each plug providing power to a subset of the plurality of electrodes on the ablation device. The method comprises the steps of connecting the first plug of the ablation device to the energy source, applying ablation energy to the tissue, unplugging the first plug from the energy source, plugging the second plug of the ablation device in to the energy source, and applying ablation energy to the tissue.

This allows ablation device construction to facilitate longer ablations by utilizing multiple connections to energy source. For example, if an energy source includes seven electrodes couple to a single plug to power seven ablation segments on the ablation device, the ablation device could include fourteen or twenty-one separate ablation segments. Each set of seven ablation segments would couple to a separate plug. In use, the first plug is inserted into the energy source and the first set of seven ablation segments is activated. Upon completion of treatment, possibly without moving the ablation device, a second region may be ablated by removing the first plug and inserting the second plug to activate the next seven ablation segments on the ablation device. This embodiment can result in a smaller less expensive energy source that is still capable of powering a long ablation device.

In yet another aspect, a method for treating heart tissue of a patient to treat a cardiac arrhythmia comprises: advancing at least one treatment member and at least one tissue securing member through an incision on the patient; removably coupling the at least one treatment member with the at least one tissue securing member; visualizing a treatment area in the patient with at least one visualization member; contacting the heart tissue of the patient with the treatment member and the tissue securing member; applying a force, through the tissue securing member, to enhance contact of the treatment member with the heart tissue; and treating the heart tissue, using the at least one treatment member. In some embodiments, and treatment member is advanced through the tissue securing member. Optionally, in some embodiments, the treatment member and the tissue securing member are advanced through a minimally invasive port applied to the patient. Another method method of the invention includes the following steps. An introducer is advanced through a first incision into the transverse sinus cavity with obturator fully inserted. At desired area near the pulmonary veins, obturator is withdrawn and the which allows the introducer to assume its pre-formed J shape reaching round the pulmonary veins, possibly also guided by contact with the pericardium. The introducer is preferably long enough to be inserted from thoracotomy into transverse sinus cavity around the pulmonary veins and out through the oblique sinus and out through the same or a different thoractomy. Another instrument is advanced through the same or different thoracotomy to grasp the distal end of the introducer. The introducer is pulled around the pulmonary veins until the distal end is outside the body of the patient. At this point, both the proximal and distal ends of the introducer are preferably outside the body of the patient. Once the ablation device is in position, suction is applied to adhere the ablation device to the tissue surrounding the pulmonary veins. Ablation energy is applied. Once treatment is complete, the ablation device can be removed.

In another aspect of the invention, a method for treating heart tissue of a patient to treat a cardiac arrhythmia comprises: verifying at least one location of a patient's cardiac parasympathetic ganglia, advancing at least one treatment member through an incision on the patient into the vicinity of the cardiac parasympathetic ganglia and applying energy to ablate at least one the cardiac parasympathetic ganglia. In a particularly preferred embodiment, the method is carried out with the assistance of a combined pacing and ablation probe. The probe has a pair of pacing electrodes that are used in a method to detect the location of the cardiac parasympathetic ganglia. Once the cardiac parasympathetic ganglia have been located, an ablation electrode on the probe can be used to apply RF ablation energy. The combined pacing and ablation probe allows the treatment method to be applied more accurately because the probe does not have to be moved or replaced with another tool to complete the ablation procedure.

Other ablation devices and methods, such as those described in US Publication 2003/0158548, which is incorporated by reference, may be suitable for use with invention described herein.

Various embodiments of the devices and methods described briefly above are further described in the appended drawings and the following detailed description. The description of specific embodiments is provided for exemplary purposes and should not be interpreted to narrow the scope of the invention as defined in the claims.

DETAILED DESCRIPTION OF THE INVENTION

Figure 1:
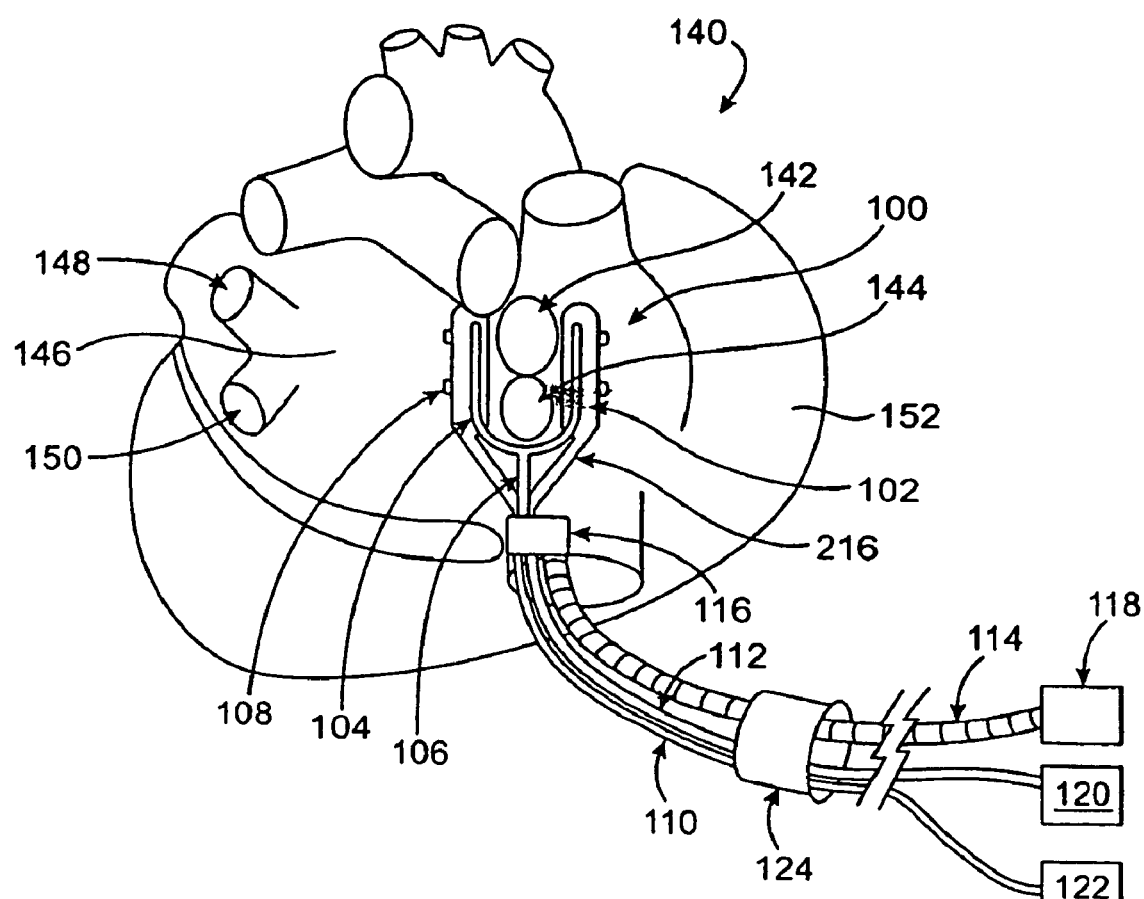
FIG. 1 is a perspective view illustration of a human heart and an ablation device in position for performing an ablation procedure, according to one embodiment of the invention.

The present invention relates generally to medical devices and methods and more specifically to devices and methods for ablating cardiac tissue for treating cardiac arrhythmias such as atrial fibrillation. Ablation of cardiac tissue in various patterns has been shown to disrupt conduction pathways in the heart to ameliorate or eliminate AF or other arrhythmias. The devices and methods will often be used to ablate epicardial tissue in the vicinity of at least one pulmonary vein, but various embodiments may be used to ablate other cardiac tissues in other locations on a heart.

Generally, ablation devices of the invention include at least one tissue contacting member for contacting a portion of the epicardial tissue of a heart, securing means for securing the ablation device to the tissue and at least one ablation member coupled with the contacting member for ablating at least a portion of the tissue. In various embodiments, the devices have features which enable the device to attach to the epicardial surface with sufficient strength to allow the tissue to be stabilized via the device. For example, some embodiments may use suction force to secure the device to epicardial tissue and stabilize a beating heart to enable a beating heart ablation procedure. In some embodiments, the preferred vacuum pressure is −200 mmHG to −760 mmHG. The suction force may be used to create a fluid gradient through the thickness of the tissue. A dynamic fluid gradient may enhance energy conduction. Other embodiments may include other optional features, such as sensors for sensing whether tissue has been ablated, a support member with an arm for connecting the device to a positioning device, cooling apparatus for cooling epicardial tissue, visualization devices and/or the like. Some embodiments of the device are introducible into a patient via minimally invasive means, such as a minimally invasive incision, sheath, trocar or the like. Ablation devices of the invention configured for use in minimally invasive procures will, in some embodiments, be longer than two feet the majority of the probe rests outside of the patient while the active ablation portion of the device is inserted via minimally invasive incision. Some embodiments will further comprise apparatus for reducing kinking of the ablation probe.

In alternate embodiments the length of the suction pods may be varied such that suction pods of more than one length are used on the same tissue contacting member. Furthermore, the suction pods may be spaced apart or placed in groupings separated by lengths of the probe or ablation device. Some or all of the length of the ablation device used to emit ablation energy may not include any suction pods. In such embodiments an insulated member may cover the majority of the geometry of the ablation device such that only areas contacting target tissue can emit energy that will penetrate the tissue. This feature may protect surrounding tissues from unintentional ablation. Positioning the ablation member within an insulating tissue contacting member provides a safety margin protecting adjacent tissue that is not intended to be ablated. The insulated member may includes lumens for delivering saline to lower impedance or increase conductivity or other substance to improve performance and efficiency of energy emission. In other embodiments, the ablation device may include indicators for identifying which ablation element is to be activated. For example, the ablation device may include different colored lines to assist the user in distinguishing the orientation and alignment of the ablation device.

The invention also includes ablation systems which include an ablation energy source for providing energy to the ablation device. The ablation energy source of the invention is particularly suited for use with ablation apparatus as described herein using RF energy, but is not limited to such use, and other kinds of ablation energy sources and ablation devices may be useable in the invention. A typical RF ablation system comprises a RF generator which feeds current to an ablation device, including those described in this application, containing a conductive electrode for contacting targeted tissue. The electrical circuit is completed by a return path to the RF generator, provided through the patient and a large conductive plate, which is typically in contact with the patient's back.

In some embodiments, the ablation system is configured to recognize the kind of ablation device connected by including keyed plugs, which describes specialized socket shapes configured to accept only plugs which are manufactured with the matching shape. The energy source includes predetermined settings appropriate for the kind of device that is accepted by that socket.

In another embodiment, the ablation system of the invention includes apparatus for recognizing the kind of device that has been coupled to the energy source and for automatically adjusting various settings to accommodate the detected device.

Methods of the invention generally include contacting a device with epicardial tissue, using a tissue contacting member on the device to secure the device to the tissue, and ablating the tissue with an ablation member on the device. In some embodiments, the method further includes additional steps such as positioning the device on the epicardial tissue, stabilizing cardiac tissue, cooling cardiac tissue, positioning the device using a positioning device, visualizing epicardial tissue with an imaging device and/or the like. Again, although much of the following description focuses on embodiments used to treat AF by ablating epicardial tissue near one or more pulmonary veins on a human heart, the devices and methods may be used in veterinary or research contexts, to treat various heart conditions other than AF, to ablate cardiac tissue other than the epicardium and/or in any other suitable manner or context.

Referring now to FIG. 1, an ablation device 100 is shown in position for ablating epicardial tissue on a human heart 140. A top view of ablation device 100 is shown, the visible components of device 100 including a tissue contacting member 102 coupled with a suction connector 216 and a support member 104 having a support arm 106. Tissue contacting member 102 also includes multiple artery securing arms 108 for securing one or more coronary arteries. Suction connector 216 is coupled with a suction cannula 112, which in turn is coupled with a suction source 120. Support arm 106 is coupled via a clamp 116 to a positioner 114, which in turn is coupled to a stabilizing device 118 for stabilizing positioner 114. Finally, an ablation member (not visible) of ablation device 100 is coupled, via a wire 110, to an energy source 122. In various embodiments, ablation device 100 may be introduced into a patient through a minimally invasive introducer device, such as a sheath 124, trocar or the like, as is represented in FIG. 1 by a simplified representation of sheath 124.

In an alternate embodiment, the artery securing arms 108 may instead be configured to grasp a second ablation member, thereby allowing ablation to occur outside of the region covered by the tissue contacting member. In this embodiment the features 108 are instead auxiliary securing arms. Although example auxiliary securing arms are shown only in FIG. 1, this feature could be used on other ablation device embodiments.

In FIG. 1, ablation device 100 is shown in a position partially encircling the right superior pulmonary vein 142 and the right inferior pulmonary vein 144. As will be described in further detail below, such a position is only one possible configuration for treating heart 140. In other embodiments, for example, both of the right pulmonary veins 142, 144 may be completely encircled, only one may be partially or completely encircled, the left superior 148 and/or left inferior 150 pulmonary veins may be partially or completely encircled and/or various patterns may be ablated on the left atrium 146, the right atrium 152 and/or the right and left ventricles (not labeled). Any ablation pattern suitable for heart treatment may be accomplished by one or more embodiments of the present invention. Thus, the following descriptions of various embodiments should not be interpreted to narrow the scope of the invention as set forth in the claims.

Generally, ablation device 100 includes at least one tissue contacting member 102 coupled with at least one ablation member (not shown in FIG. 1). One embodiment of a device which may be used as tissue contacting member 102 is described in U.S. patent application Ser. No. 60/182,048, filed on Feb. 11, 2000, the entire contents of which is hereby incorporated by reference. Ablation device 100 shown in FIG. 1 actually includes two tissue contacting members 102, one on either side of the right pulmonary veins 142, 144. Tissue contacting members 102 may be coupled together via support member 104 and suction connector 216. In other embodiments, some of which will be described below, tissue contacting member 102 may include only one member, more than two members, a coupling member disposed between multiple arms and/or the like. Alternatively, tissue contacting member 102 may be conical, linear, shaped as a flat pad or a flat elongate member or may have any other suitable configuration. Additionally, tissue contacting members 102 may have any suitable size and dimensions. For example, in FIG. 1, tissue contacting members 102 and device 100 in general have a shape and dimensions to contact and ablate epicardial tissue on heart 140 in a pattern partial encircling the right pulmonary veins 142, 144. Many other configurations and sizes are possible, as described further below.

Tissue contacting members 102 may be manufactured from any suitable material, such as a polymer, plastic, ceramic, a combination of materials or the like. In one embodiment, for example, tissue contacting members 102 are manufactured from a liquid molded rubber. In some embodiments, the material used to make tissue contacting members 102 is chosen to allow the members 102 to be at least partially deformable or malleable. Deformable tissue contacting members 102 may allow ablation device 100 to be inserted into a patient and/or advanced to a surgical site within the patient via a minimally invasive incision or a minimally invasive introducer device, such as sheath 124. Deformable tissue contacting members 102 may also allow device 100 to conform to a surface of heart 140, to enhance ablation of epicardial or other cardiac tissue. In some embodiments, tissue contacting members 102 include one or more artery securing arms 108, for securing, exposing and/or occluding one or more coronary arteries via silastic tubing attached between the artery and securing arm 108. Securing arms 108 are generally made of the same material(s) as tissue contacting members 102 but may also suitably comprise other materials.

In some embodiments the ablation device may be inserted minimally invasively under stress, and is configured to conform to the topography or anatomy of the tissue to be treated when relaxed. This feature may enhance the adherence of the ablation device to the tissue because the suction is not working against resistance of the ablation device to conforming to the desired shape.

Thus, some embodiments the preferred features of the material used to manufacture tissue contacting member 102 may further include one or more of the following characteristics: the material provides electrical or thermal insulation, the material is flexible to facilitate remote advancement via torturous pathways, the material has shape memory allowing large elastic deformation of the tissue contacting member but also allowing the tissue contacting member to return to a pre-formed shape in a relaxed configuration, the material may be translucent or transparent to help the user see the position of the ablation probe, the material may be lubricious to facilitate insertion and placement, and the material allows thin walled construction of the tissue contacting member so that collapse of the tissue contacting member can be seen to confirm the operation of the vacuum when activated.

In some embodiments, tissue contacting members 102 are coupled with support member 104. Support member 104 may be made of any suitable biocompatible material, such as titanium, stainless steel, nickel titanium alloy (Nitinol) or the like. Support member 104 may be coupled with tissue contacting members 102 by any suitable means, such as but not limited to one or more adhesive substances, placement of a portion of support member 104 within a sleeve on tissue contacting members 102 or a combination of both. Like tissue contacting members 102, support member 104 may also be malleable or deformable to allow for insertion of ablation device 100 through a minimally invasive sheath 124 and/or for enhancing conformability of device 100 to a surface of heart 140. Support member 104 typically includes at least one support arm 106 or similar protrusion or multiple protrusions for removably coupling ablation device 100 with positioner 114 or one or more other positioning devices. Positioner 114, for example, may comprise a flexible, positioning arm, with attachment means such as clamp 116 for attaching to support arm 106 and stabilizing device 118 for stabilizing positioner 114. For example, a flexible, articulating positioner 114 may be of the type which rigidities when tensile force is applied, such as via a tensioning wire. Any other suitable positioner 114 may alternatively be used. In other embodiments, device 100 may not include support member 104. Such devices 100 may incorporate a connection arm onto a tissue contacting member 102, may be positioned on heart 140 using a positioning device inserted through a separate incision, or may be positioned or manipulated by a physician or other user via any other suitable means.

Tissue contacting members 102 may also be coupled with one or more suction cannulas 112 to provide suction for enhancing contact of ablation device 100 with epicardial tissue. In various embodiments, tissue contacting members 102 may be directly coupled to one or more cannulas 112 or may be connected via one or more suction connectors 216. In FIG. 1, a V-shaped suction connector is used to couple the two tissue contacting members 102 with a common cannula 112. Cannula 112, in turn, is connected to suction source 120, which may be a conventional wall suction or stand-alone suction source. Generally, cannula 112 may be any suitable conventional cannula 112, which are well known to those skilled in the art. Suction connector 216 is typically comprised of the same material(s) as tissue contacting members 102, but may also be made of a material or materials used to make cannula 112. Suction connector 216 may further include a nozzle 218 for connecting to cannula 112.

Ablation device 100 also includes at least one ablation member 210. Ablation member 210 typically receives energy from a separate energy source 122, although ablation members 210 with internal energy sources are also contemplated. Where a separate energy source 122 is used, ablation member 210 may be coupled with source 122 by any suitable means. In one embodiment, for example, ablation member 210 may be coupled to energy source 122 with wire 110. Wire 110 may be any suitable connector, such as fiber optic cable, electric cable, coaxial cable, ultrasound transmission device or the like. As is described further below, any suitable energy may be provided by energy source 122 for ablation and any means for transmitting energy to ablation member 210 is contemplated within the scope of the invention. In some embodiments, for example, energy may be transmitted remotely, so that no wires or other similar connecting devices are required. In other embodiments, radio frequency energy may be provided by an RF energy source and transmitted to ablation member 210 via conventional electrical wire(s) 110.

Generally, ablation member 210 may be configured to transmit energy of any suitable quantity or force. For example, in some embodiments sufficient energy will be transmitted through ablation member 210 to ablate only epicardial tissue on a heart. In other embodiments, sufficient energy may be transmitted to cause one or more layers beneath the epicardial tissue to be ablated. In some embodiments, for example, one or more transmural lesions (across the entire wall of the heart) may be ablated. Typically, an amount of energy transmitted through ablation member 210 will be adjustable to create a desired ablation depth.

As mentioned briefly above, a minimally invasive introducer sheath 124, trocar or other minimally invasive device may be used for introducing one or more of the components shown in FIG. 1 into a patient. In some embodiments, a sheath need not be used and instead only a minimally invasive incision is used. In other embodiments, multiple minimally invasive incisions and/or sheaths 124 may be used for introducing various devices into a patient. For example, one sheath 124 may be used for introducing ablation device 100 and another sheath 124 may be used for introducing positioner 114. Although devices and methods of the present invention are often suitable for minimally invasive procedures, they may also typically be used in open surgical procedures, either with or without cardiopulmonary bypass, in various embodiments.

Figure 2:
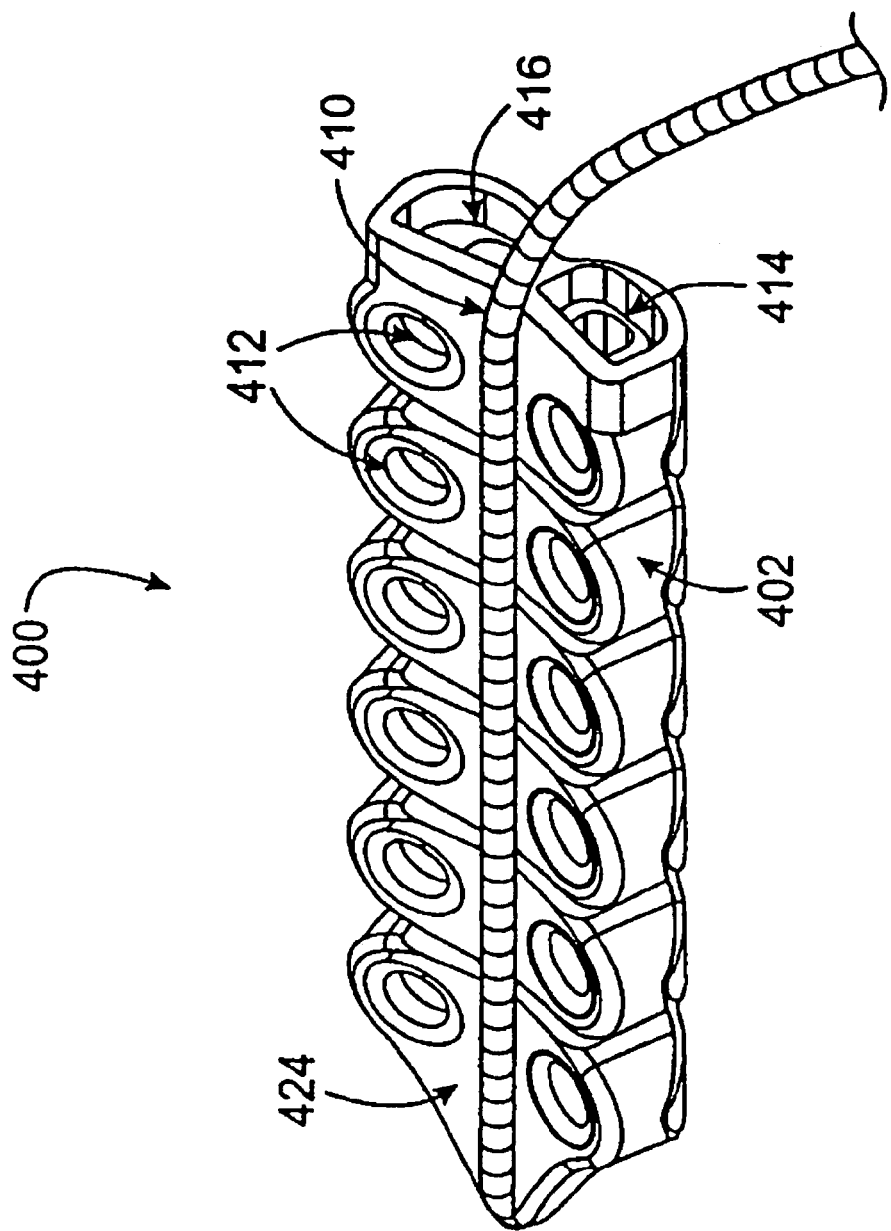
FIG. 2 is a perspective view of a flexible, elongate ablation device with two rows of suction apertures, according to one embodiment of the invention.

Referring now to FIG. 2, another embodiment of ablation device 400 comprises a largely flexible device which includes a tissue contacting member 402 and an ablation member 410. Tissue contacting member 402 may be made of any suitable, flexible material, such as a silicone, polyurethane, polycarbonate, another suitable polymer or combination of polymers or the like. Tissue contacting member 402 generally includes a tissue contacting surface 424 having multiple suction apertures 412. Tissue contacting surface 424 may be slightly concave (as shown), flat or may have any other suitable shape. Suction apertures 412 are disposed in two parallel lines, one line on either side of ablation member 410 and communicate with suction lumens 414 and 416. Suction lumens 414, 416 may be coupled with one or more suction cannulas or similar devices for providing suction force through suction apertures 412. Other embodiments may include one common suction lumen for connection to a suction cannula.

As with various embodiments described above, any suitable ablation means may be used as ablation member 410 in device 400. In the embodiment shown, ablation member 410 comprises a linear radio frequency coil. Ablation member 410 may extend beyond the length of tissue contacting member 402, either in a proximal or distal direction and may be coupled with a source of energy via a wire (not shown) or other connection device. In various embodiments, one or more of the features described above, such as support members, retractable ablation elements, sensors, cooling members, positioning arms and/or the like may be incorporated into or used with ablation device 400. Alternatively, ablation device 400 may simply include tissue contacting member 402 and linear ablation member 410. Such an embodiment may be advantageous for introduction through a narrow, minimally invasive introducer sheath, due to the device's flexibility and relatively small size. In one embodiment, for example, device 400 may measure approximately 3.25 in. in length and approximately 0.9 in. wide and may further be deformable to a narrower configuration for insertion through a sheath. Furthermore, device 400 may be sufficiently flexible to conform to curved surfaces of heart 140, allowing for enhanced contact with and ablation of epicardial tissue. Finally, it may sometimes be advantageous to ablate epicardial tissue in a linear pattern or in multiple line. Ablation device 400 may be movable, to allow ablation in a first line, a second line, a third line and/or the like.

Figure 3:
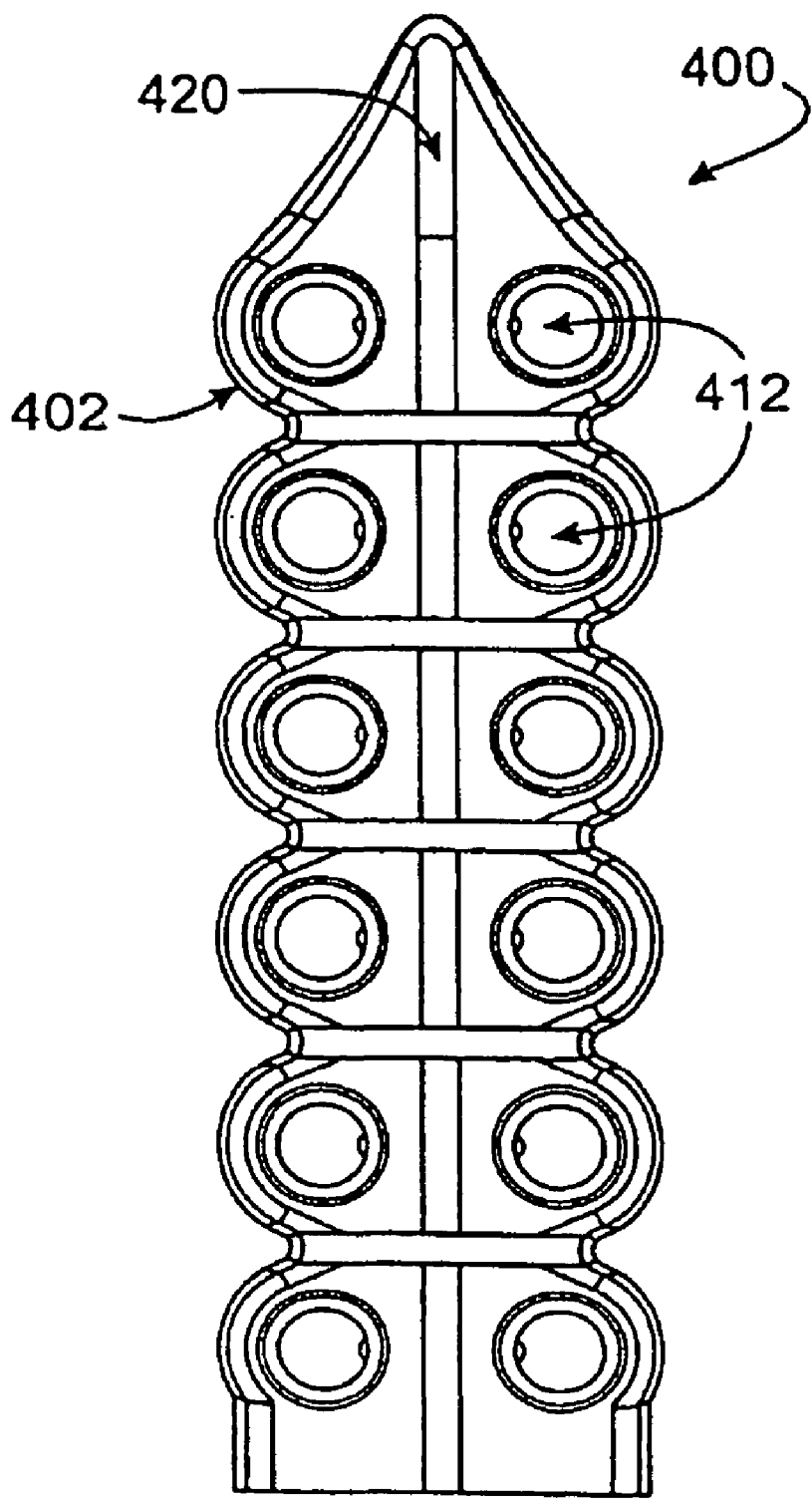
FIG. 3 is a bottom-surface view of the ablation device as shown in FIG. 2, with the ablation member removed.

Referring now to FIG. 3, a bottom-side view of ablation device 400 is shown with ablation member removed. It can be seen that tissue contacting member 402 may include a trough 420 in which ablation member 410 may be positioned. In some embodiments, ablation member 410 may be a removable piece which may be removably attached to tissue contacting member 402, at least partially disposed within trough 420, so that one ablation member 410 may be used with multiple tissue contacting members 402, one after another, for example if tissue contacting members 402 are single-use, disposable devices.

In some apparatus and methods of the invention, once the tissue contact member is positioned and suctioned on to the heart, the ablation device 400 may also be slid within the trough 420 in the tissue contact member 402 so that the energy emitting section of the ablation member 410 may be positioned as a separate step from the step of positioning the tissue contacting member 402. It is also possible to position the tissue contacting member 402 separately from the ablation member 410, then in a later step, slide the ablation member 410 into the tissue contact member 401. In some embodiments, an ablation member 410 with a short energy emitting section may be moved along a trough 420 in the tissue contact member 401 so that the ablation device 400 can create long lesions, perhaps longer than the ablation section of the ablation member 410, with minimal manipulations of the device within the track.

Figure 4:
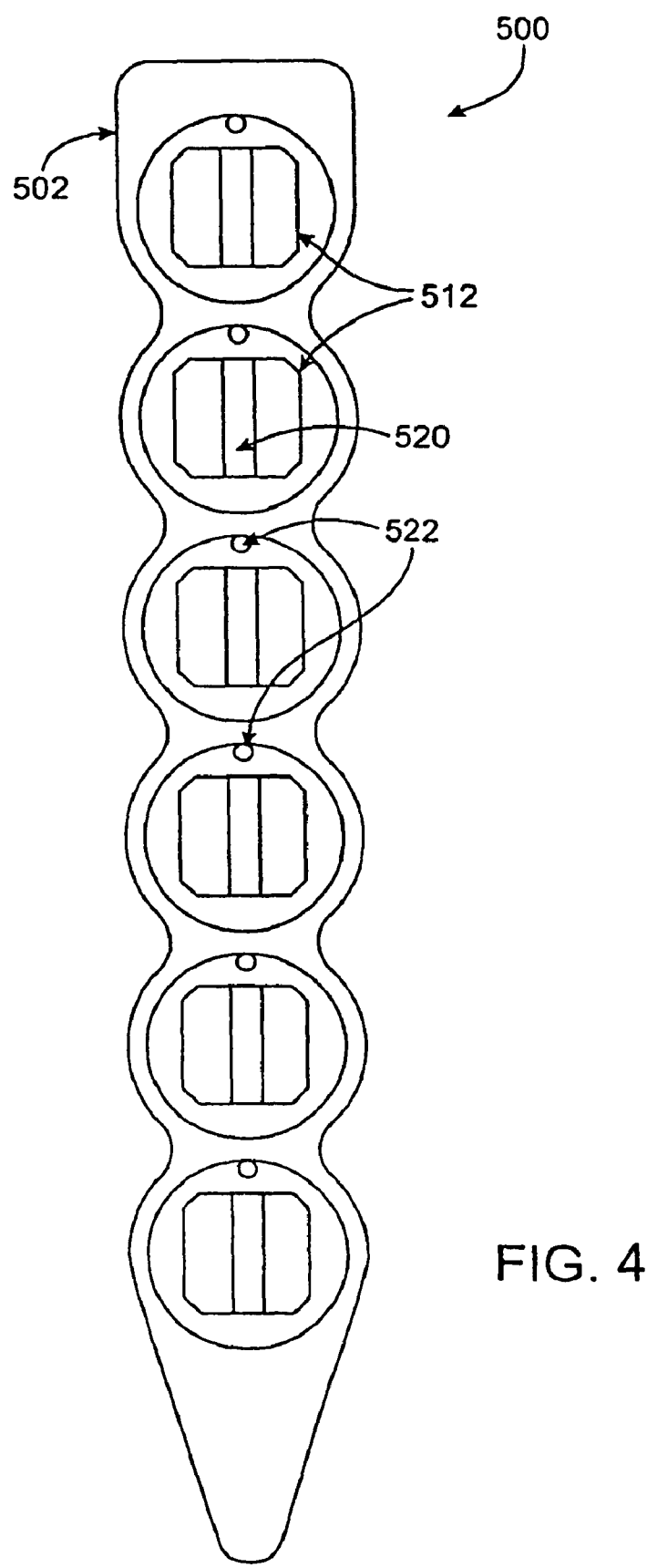
FIG. 4 is a bottom-side view of a flexible, elongate ablation device with one row of suction apertures, according to one embodiment of the invention.

Using a single placement of the tissue contacting member may enhance continuity of ablation lesions. Not having to move the ablation device between discrete ablation cycles, and instead only moving the ablation member within the tissue contacting member, insures that adjacent ablation segments are contiguous with no ablation gaps. Avoiding the creation of gaps can be critical to insure electrical isolation of desired tissue areas, and may also decrease procedure time by not requiring the surgeon to verify overlap of adjacent ablation lesions FIG. 4 shows yet another embodiment of ablation device 500, including a tissue contacting member without an ablation member being shown. Device 500 is similar to ablation device 400, but tissue contacting member 502 has one row of suction apertures 512 rather than two and ablation member, placed in ablation trough 520, overlays suction apertures 512. Suction holes 522 shown in suction apertures 512 demonstrate that the apertures sometimes include both a depressed or concave surface and one or more holes communicating with a suction lumen. The embodiment of ablation device 500 in FIG. 5 may be advantageous for forming one or more linear ablations on heart 140 when there is minimal space in which to manipulate device 500 and/or when a narrow, minimally invasive incision or sheath is desired for insertion of device 500. Device 500 may be manufactured from any suitable material or combination of materials, such as those described above, may use any suitable form of ablation member and may include various additional features as desired.

Figure 5A:
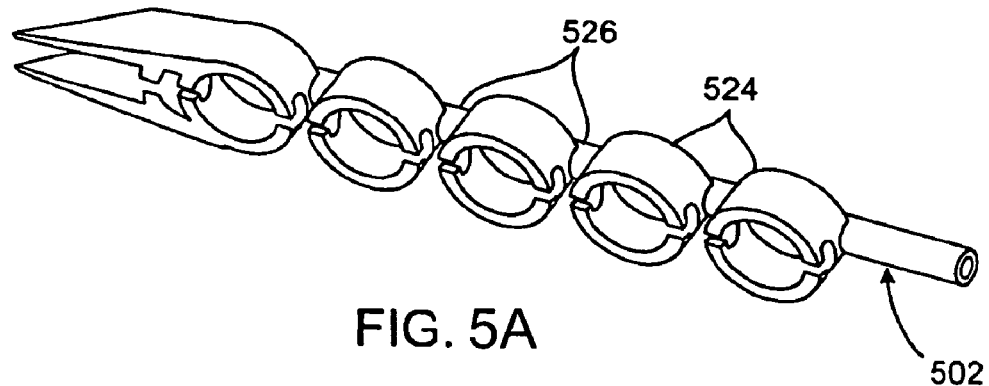
FIGS. 5a, 5b, and 5e are perspective views of another embodiment of a flexible, elongate ablation device with one row of suction apertures, separated by flexible joining members.
Figure 5B:
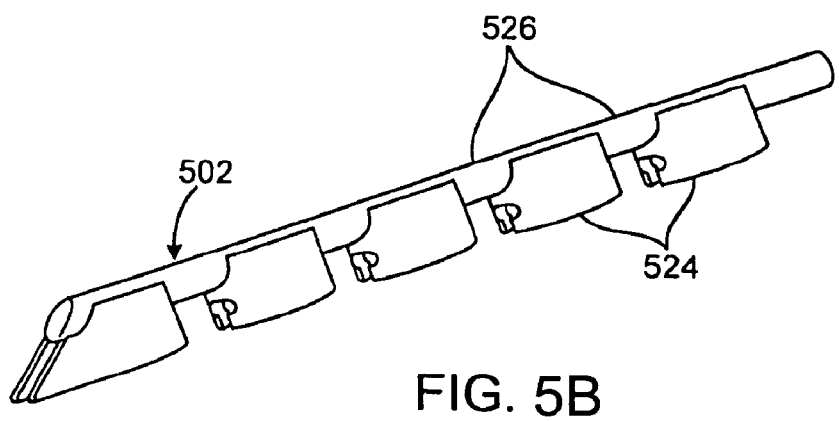
Figure 5C:
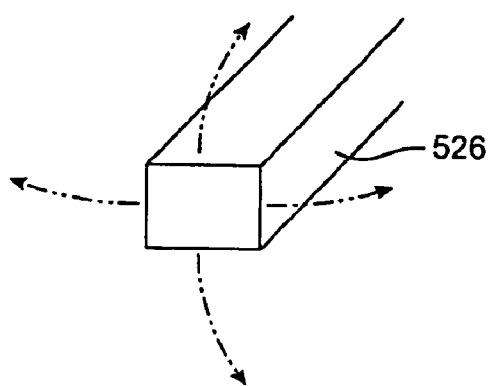
FIGS. 5c and 5d show several alternate cross sections of the flexible joining members of FIGS. 5a and 5b.
Figure 5D:
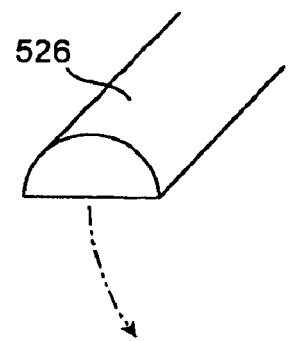
Figure 5E:
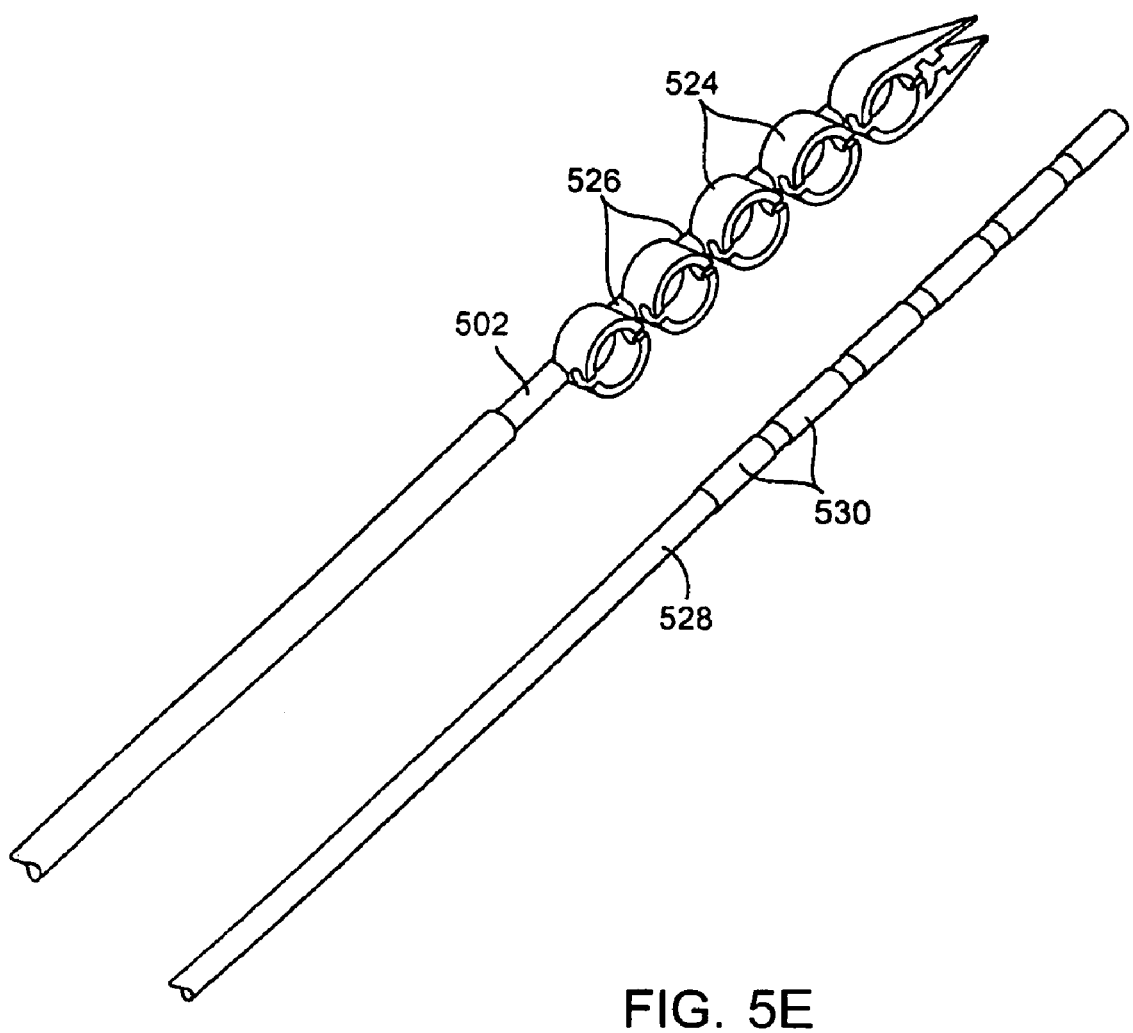

FIG. 5a is a bottom perspective view of an alternate another embodiment suction pods 524 spaced some distance apart and joined by a flexible joining members 526, which may also be used to provide a channel for a vacuum lumen. The distance between the suction pods 524 and the flexibility of the joining members 526 between the suction pods 524 has been found to increase the ability of the tissue contacting member 502 to bend in sharp turns. In FIGS. 5a and 5b, the joining members 526 are cylindrical in cross section, which may improve the overall flexibility of the ablation device 500 in all directions. The flexibility can be varied as desired by changing the thickness, shape, and size of the joining members 526 between the suction pods 524, and by varying the flexibility of the material used to fabricate the joining members 526. For example, FIGS. 5c and 5d show example alternate joining member 526 cross sections. The square cross section of FIG. 5c may allow bending in X and Y axes, but may resist axial rotation. The example cross section shown in FIG. 5d may allow bending in a downward vertical direction, but may resist bending in lateral directions. FIG. 5E shows an ablation member 528 including ablation segments 530 configured for insertion in to tissue contacting member 502.

Figure 6:
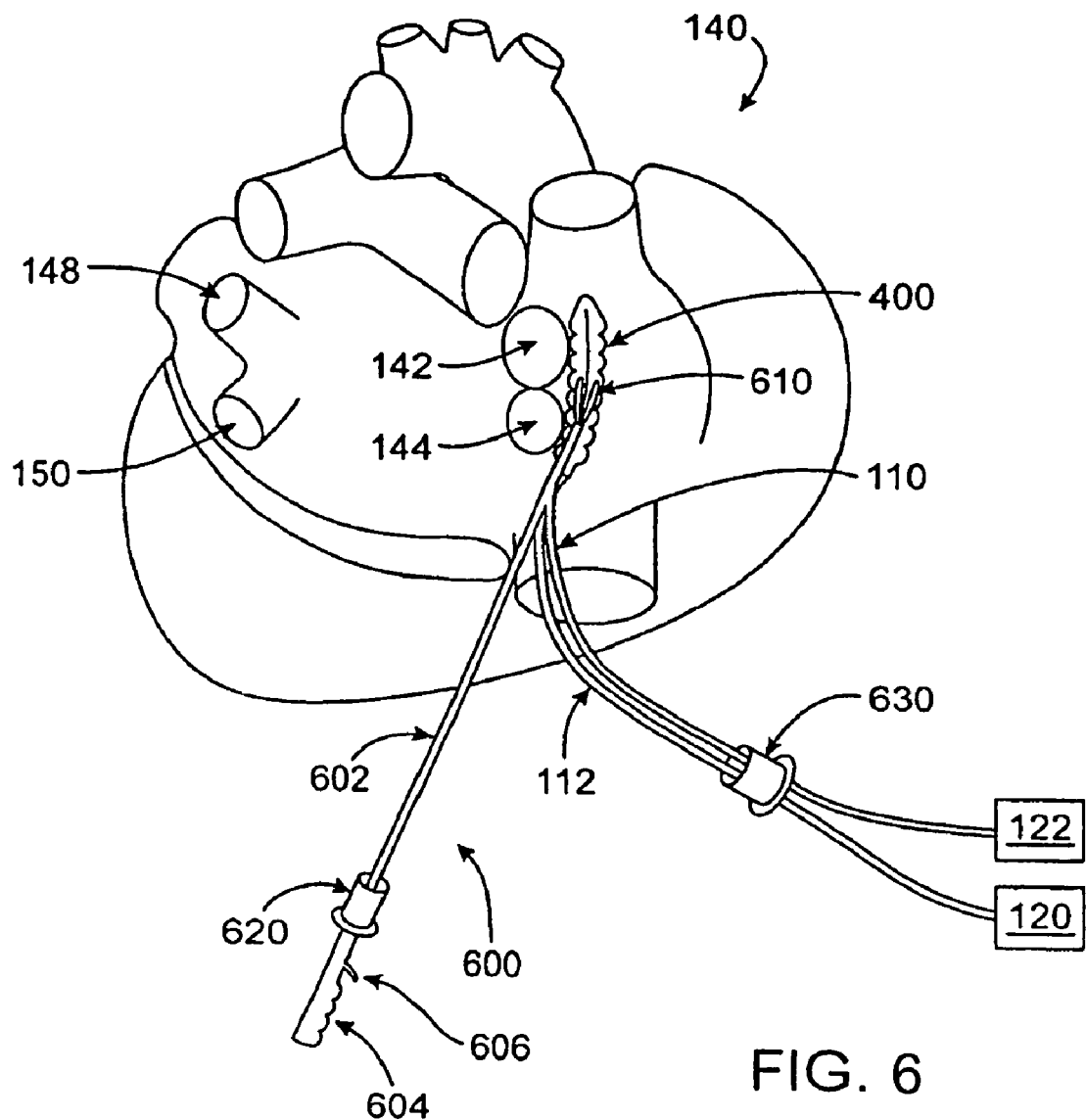
FIG. 6 is a perspective view of a human heart and an ablation device in position for performing an ablation procedure, according to one embodiment of the invention.

Referring now to FIG. 6, ablation device as described with reference to FIGS. 2 and 3 is shown in position for performing epicardial ablation on a human heart 140. Generally, ablation device 400 may be placed in any desired position on heart 140 for ablating epicardial tissue. Thus, in various embodiments device may be placed adjacent one or both of the right pulmonary veins 142, 144, adjacent one or both of the left pulmonary veins 148, 150, or in any other suitable location. Furthermore, ablation device 400 may be used to ablate tissue in a linear pattern at one location and then may be moved to ablated tissue in a linear pattern in another location. As discussed above with reference to various embodiments, ablation device 400 may be introduced into a patient via a minimally invasive device, such as a sheath 630 or trocar, and may be coupled with a source of suction 120 via a suction cannula 112 and with a source of ablative energy 122 via a wire 110 or other connective device.

Ablative device 400, as well as other embodiments of ablative devices described above, may be positioned on heart 140 via a positioning device 602 which is introduced via a second minimally invasive incision or second sheath 620. Second sheath 620 may be placed at any suitable location on the patient to allow access to ablation device with the positioning device 602. Positioning device 602 may then be introduced through sheath and advanced to the position of ablation device 400. Positioning device 602 may then be used to secure device 400, such as by opposable jaws 610 or any other suitable means, and position device 400 in a desired location on heart 140. In some embodiments, positioning device may further be used to reposition device 400 to perform ablation in multiple locations on heart 140. The proximal end of positioning device 602 may include a handle 604 for holding and manipulating device 602 and one or more actuators 606, such as a trigger for opening and closing opposable jaws 610 or other distally positioned end effectors of device 602. Examples of positioning device 602 may include, but are not limited to, conventional minimally invasive surgical devices such as laproscopic surgical devices and the like.

Figure 7:
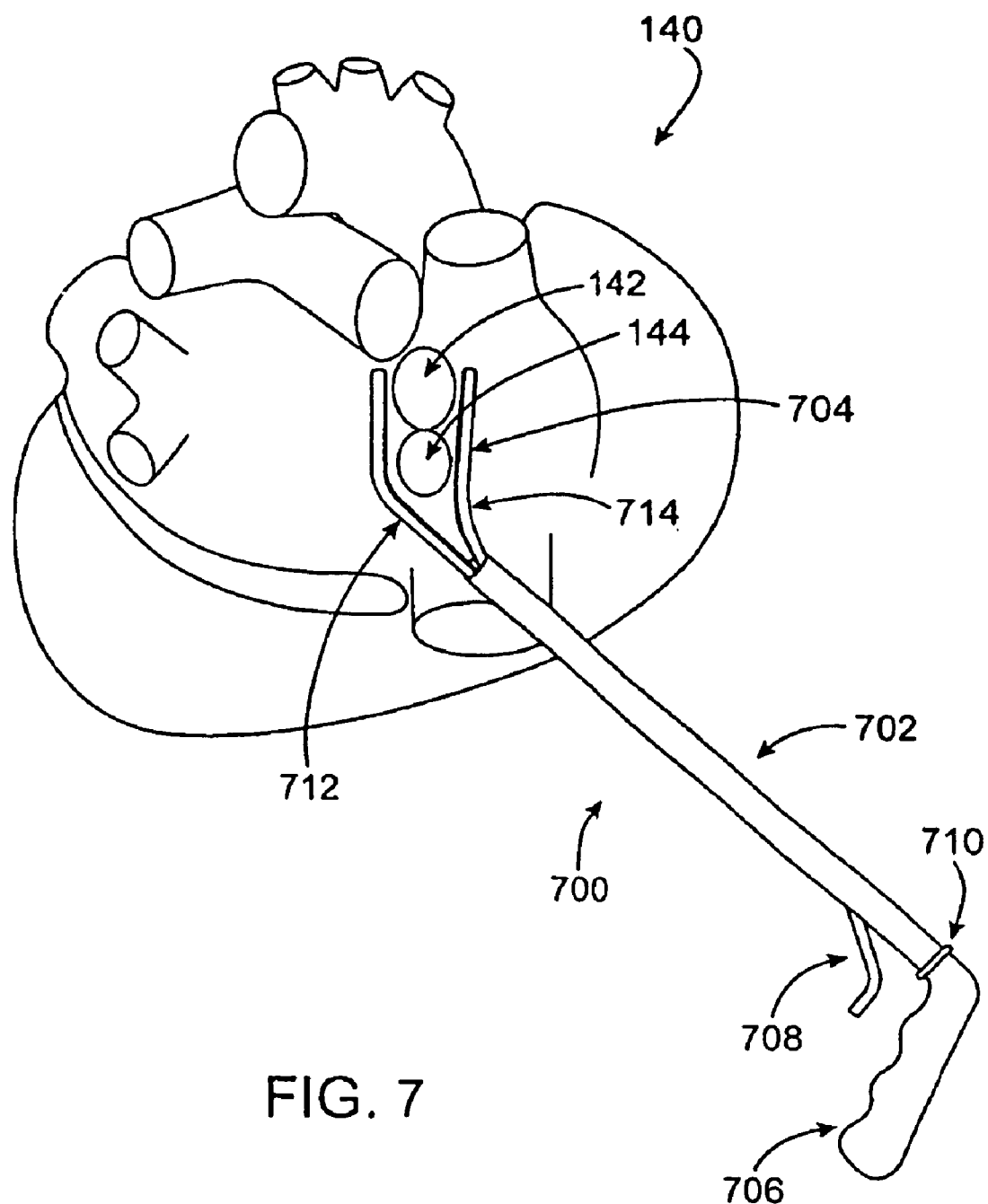
FIG. 7 is a perspective view of a human heart and an elongate shaft ablation device in position for ablating cardiac tissue, according to one embodiment of the invention.

FIG. 7 shows ablation device 700, as just described, in a position for performing an ablation procedure on epicardial tissue of heart 140. Device as shown will ablate in a pattern approximating two lines adjacent the right pulmonary veins 142, 144. It should be understood, from the foregoing descriptions of various embodiments, that jaw member 704 and ablation members 712, 714 could alternatively be configured in any other suitable shape, size or configuration to ablate in other patterns on heart 140. Additionally, device 700 may be moved to a variety of positions to ablate multiple patterns in multiple locations on the epicardial tissue.

Figure 8:
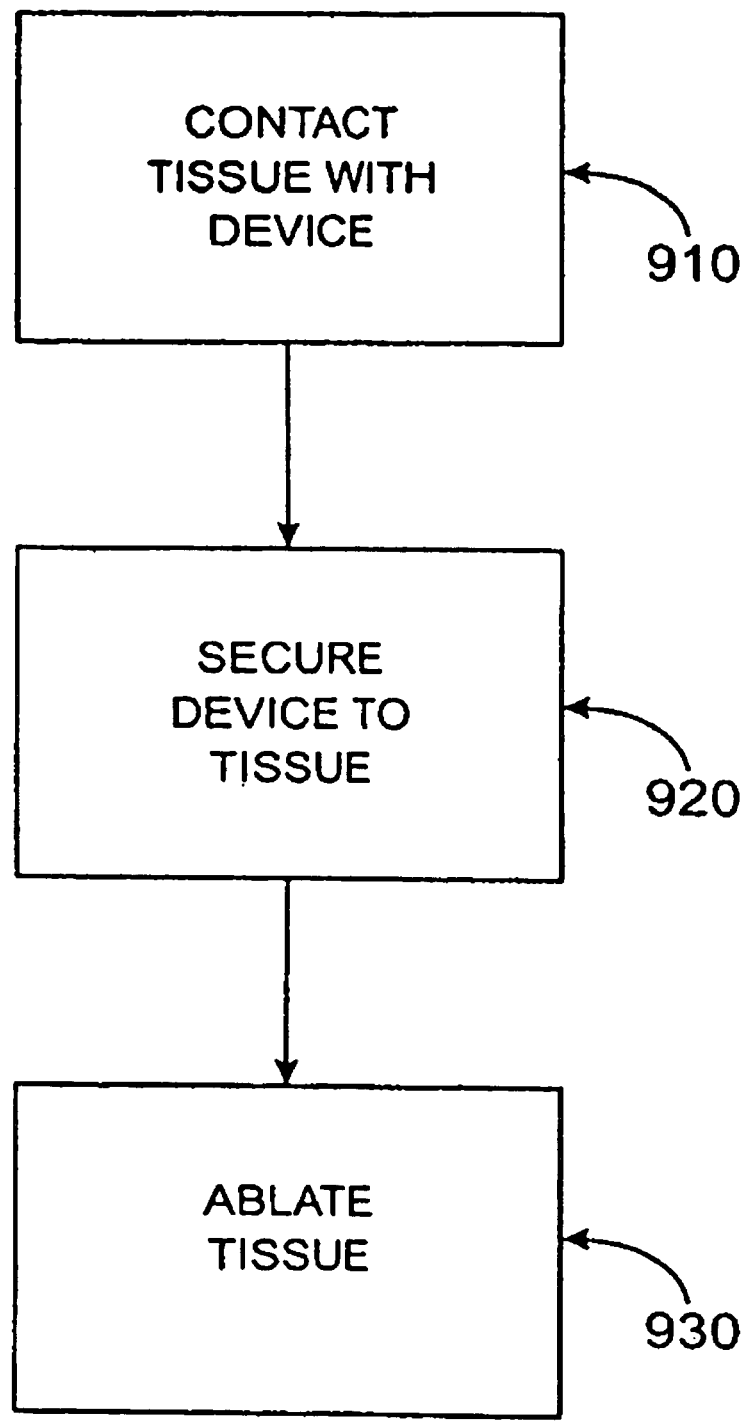
FIG. 8 is a block diagram of a method for ablating tissue according to one embodiment of the invention.

With reference now to FIG. 8, a method for ablating cardiac tissue, such as epicardial tissue, suitably includes contacting cardiac tissue with an ablation device 910, securing the device to the tissue 920 and ablating at least a portion of the contacted, secured tissue 930. Various embodiments of the invention will utilize additional steps or sub-steps of these three basic steps, but it should be emphasized that any additional steps or variations are optional. For example, in some embodiments, contacting the cardiac tissue 910 is preceded by advancing the device into the patient through a minimally invasive introducer device. Contacting the device with the tissue 910 may include positioning the device using a positioning arm or other positioning device. In some embodiments, securing the device to the tissue 920 may also comprise invaginating a portion of epicardial tissue partially within one or more suction apertures and/or may include using one or more suction apertures to dissect through fatty tissue disposed over epicardium. Securing the device 920 may also involve securing with enough force to allow stabilization and/or positioning of the heart itself. And ablation of epicardial tissue 930 may involve ablation in any location or pattern as described above with reference to the inventive devices. Therefore, the descriptions of various methods provided herein are offered for exemplary purposes only and should not be interpreted to limit the scope of the invention as described in the claims.

Other aspects of a method for ablating epicardial tissue may include imaging the epicardial tissue and an area surrounding the tissue to be ablated, using a visualization device. Such a device may be coupled with the ablation device or may be a separate imaging device. In some embodiments, an insufflation device may be inserted between the epicardium and the pericardium and insufflation fluid or gas may be introduced to form a space between the epicardium and pericardium. The space may be used to enhance visualization, allow for freer manipulation of devices near the site for ablation and the like. Another aspect may include sensing ablation of epicardial tissue with one or more sensors, as described above. In some embodiments, tissue may optionally be cooled via a cooling member and/or irrigation of fluid into contact with the tissue. Finally, the actual ablation of epicardial tissue may be accomplished with any suitable ablation member and form of energy, including RF, thermoelectric, cryogenic, microwave, laser, ultrasound or the like. In one embodiment, ablation is achieved and/or enhanced by delivery of one or more drugs to the tissue.

The method may further include the steps of using visual and audible cues to verify the ablation device is adhered to tissue. For example the user can hear a suction sound or 'whistle' when the suction has been activated and the ablation device is not correctly adhered. Also, the user can hear vacuum pump elevate as vacuum increases. In some embodiments, the user can visually observe the tissue contacting member collapse when the ablation device is correctly adhered and suction is activated.

Figure 9:
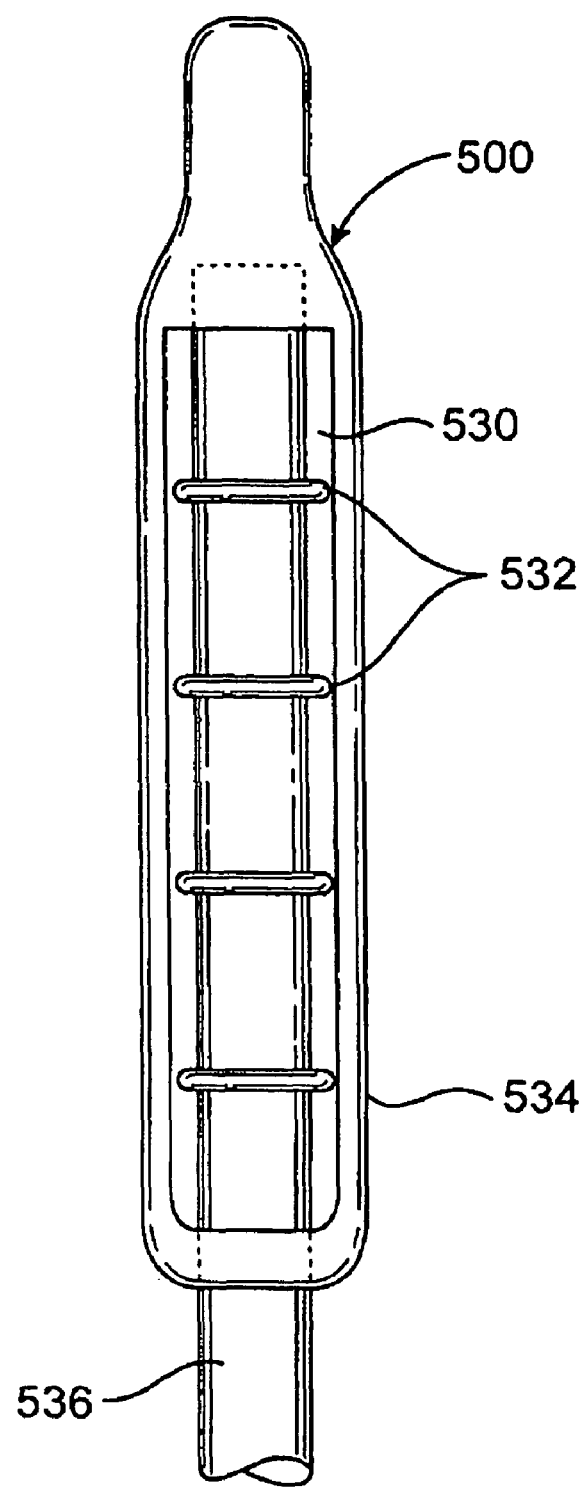
FIG. 9 is an embodiment of the invention including an elongated tissue contact member, built in accord with the invention.

In general, any number of suction pods may be used in the invention, and the number used may depend on the procedure that is to be performed. For example, FIG. 9 shows an embodiment of the ablation device 500 including a tissue contact member 534 with only a single elongated suction pod 530. In this embodiment, the suction pod 530 extends a selected length of the ablation member 536 and includes graspers 532 to hold the ablation member 536 within the suction pod 530. Any desired mechanism for holding the ablation member 536 may be used. For example, the graspers 532 may be narrow channel sections in which the ablation member 536 may be snapped into place, or the graspers 532 may be loops through which the ablation member 536 is slid into place.

In further embodiments, the ablation device may be configured to allow the ablation member to extend beyond the edge of the tissue contacting member to allow for ablation to occur outside of the region covered by the tissue contacting member.

Figure 10A:
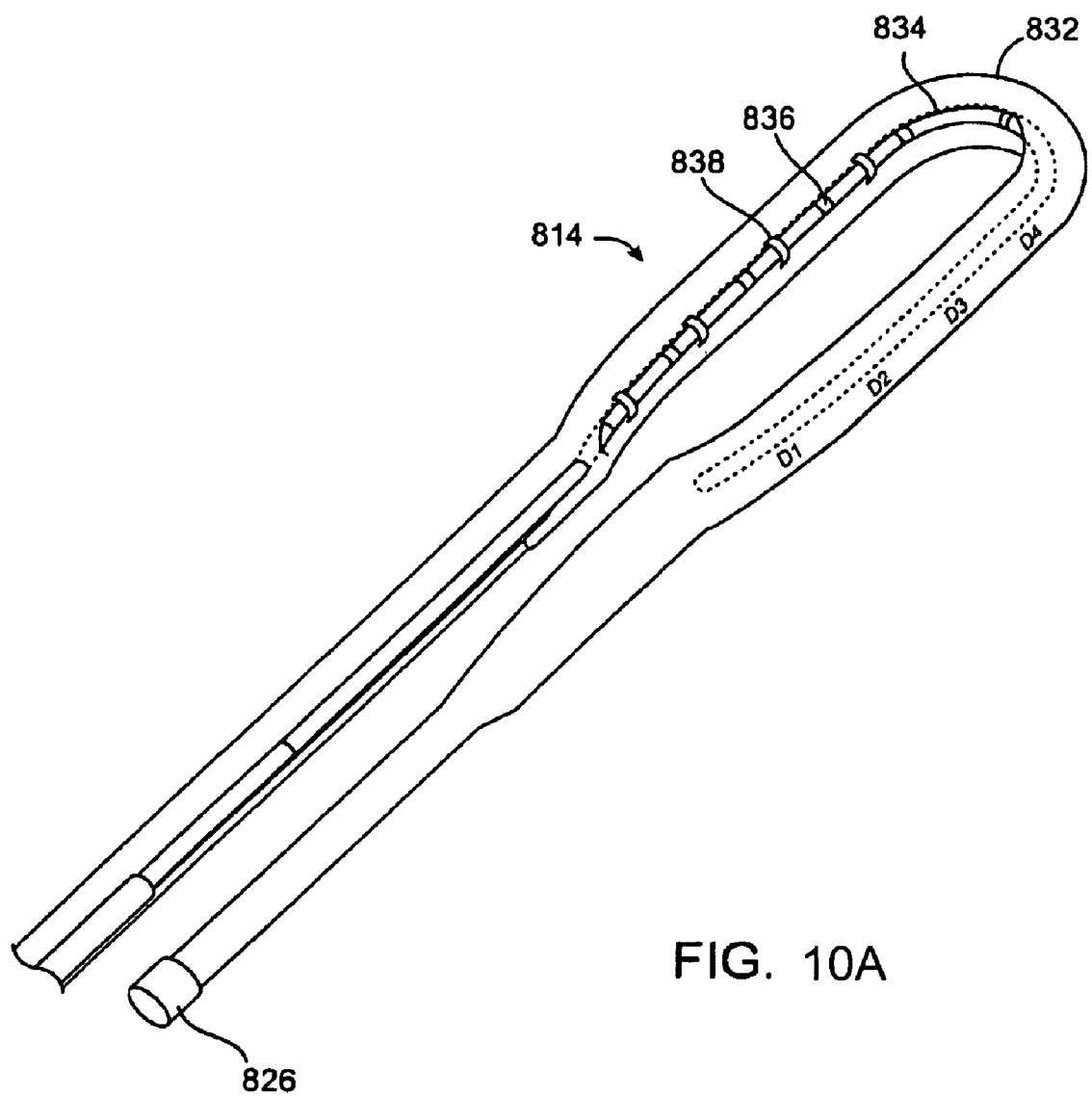
FIGS. 10a and 10b is an example ablation device in accord with the invention, and an introducer for use with the ablation device.
Figure 10B:
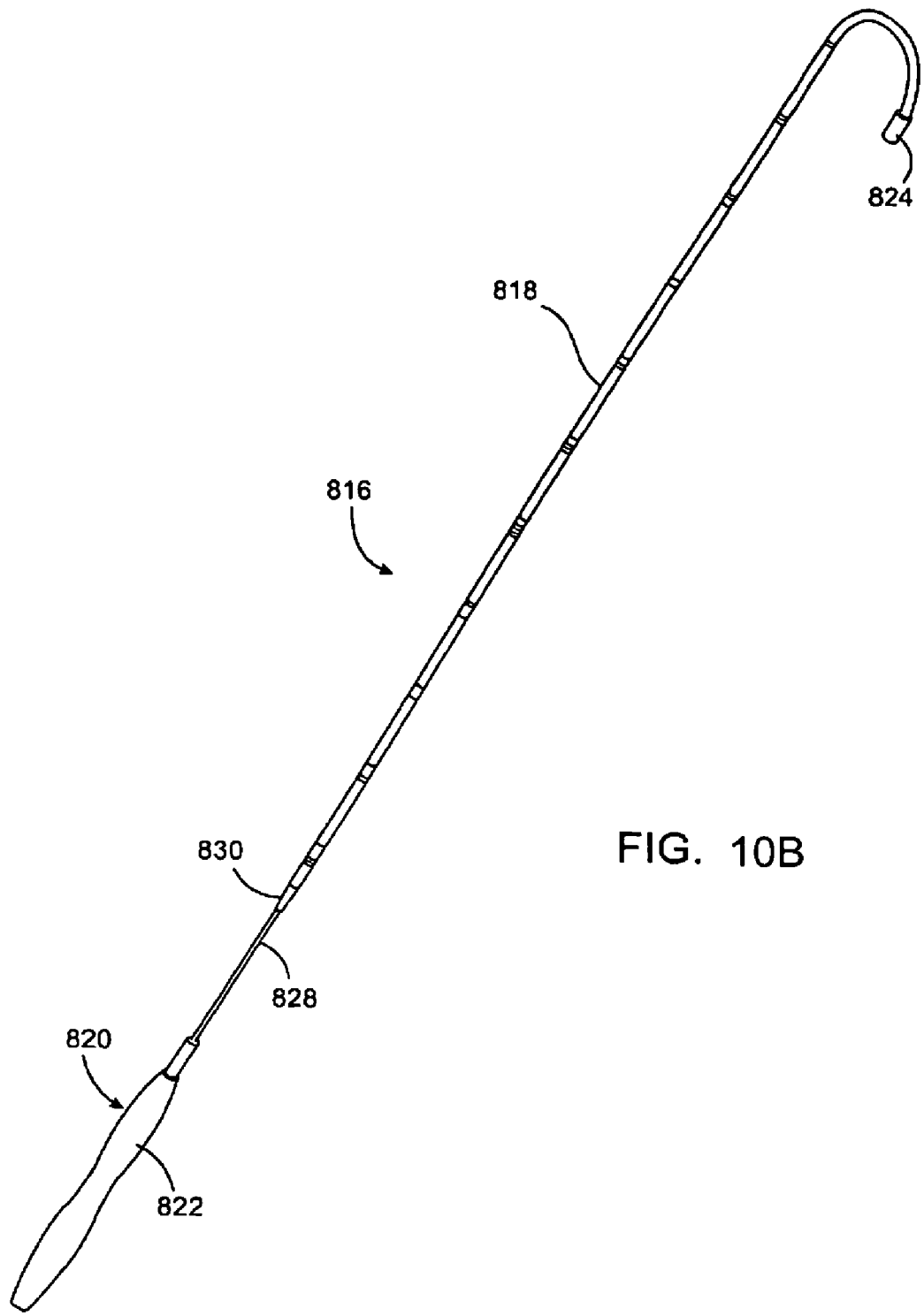

Another apparatus and method of the invention includes the following. Referring to FIGS. 10a and 10b. In some embodiments, the ablation device 814 may be deployed using an introducer 816 (best seen in FIG. 10b). The introducer 816 in this embodiment comprises a tube 818 that is pre-bent into a J shape. An obdurator 820 with a handle 822 and a shaft 828 which is inserted in to the tube 818 with the shaft 828 extending substantially through the length of the tube 818. When the obdurator 820 is removed, the tube 818 returns to its pre-bent J shape.

A distal end 824 of introducer 816 has a designate region for grasping. A selected instrument may be introduced through a the same or a second incision to grasp the distal end 824 of the introducer 816 to pull the distal end 824 of the introducer 816 outside the body of the patient. The distal end 826 of the ablation device 814 of FIG. 10a is attached to the proximal end 830 of the introducer 816. The introducer 816 is then withdrawn until the ablation device 814 is properly positioned.

In the example embodiment of the ablation device 814 seen in FIG. 10a, the ablation device 814 includes a tissue contacting member 832 including a single suction pod 834. An ablation member 836 extends through the length of the tissue contacting member 832 and includes graspers 838 to hold the ablation member 836 within the suction pod 832. Once the treatment is complete, the ablation device 814 may be decoupled from the energy source and pulled out.

An example method for using the invention described above includes the following steps. An introducer is advanced through a first incision into the transverse sinus cavity with obturator fully inserted. At desired area near the pulmonary veins, obturator is withdrawn and which allows the introducer to assume its pre-formed J shape reaching round the pulmonary veins, possibly also guided by contact with the pericardium. The introducer is preferably long enough to be inserted from thoracotomy into transverse sinus cavity around the pulmonary veins and out through the oblique sinus and out through the same or a different thoracotomy. Another instrument is advanced through the same or different thoracotomy to grasp the distal end of the introducer. The introducer is pulled around the pulmonary veins until the distal end is outside the body of the patient. At this point, both the proximal and distal ends of the introducer are preferably outside the body of the patient.

The proximal end of introducer is attached, possibly with luer fitting, to the distal end of an ablation device. Indication markers and lines on introducer and on the ablation device can be used to assist the user in properly positioning the ablation device. In a preferred embodiment, circumferential indication markers on the introducer are used as depth measurements, and an indication stripe on the surface of the introducer are aligned with similar markings on the ablation device to insure that the ablation device will be facing properly when inserted.

In this method, the introducer preferably has torsional rigidity to facilitate steerability. Further, the introducer is preferably a highly visible color for endoscopic visualization and distinguishing from natural anatomical colors.

Once the ablation device is in position, suction is applied to adhere the ablation device to the tissue surrounding the pulmonary veins. Ablation energy is applied. Once treatment is complete, the ablation device can be removed.

Figure 11B:
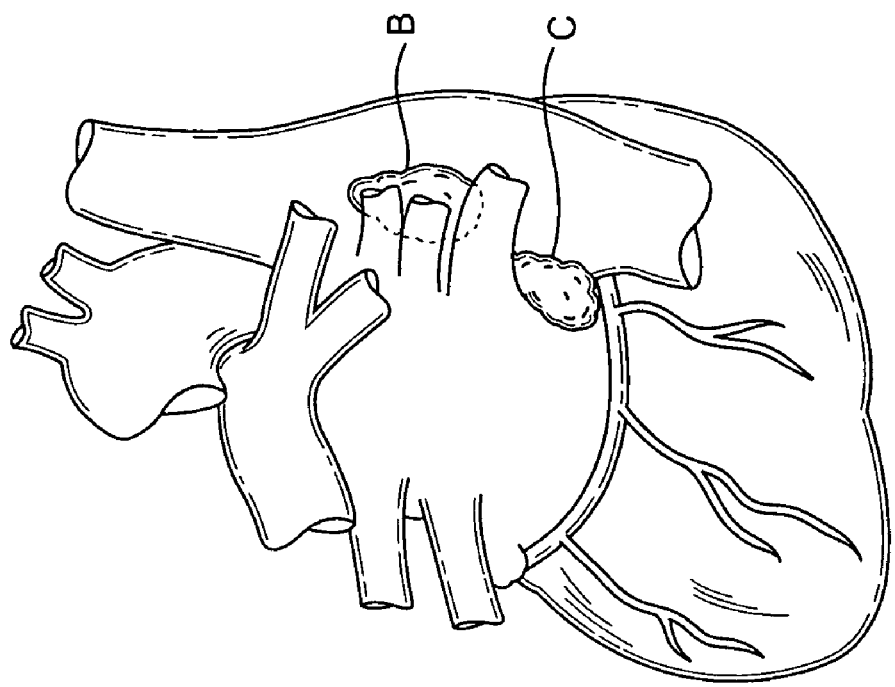
FIGS. 11A and 11B show the locations of the para-cardiac fat pads where the cardiac parasympathetic ganglia are located.
Figure 11A:
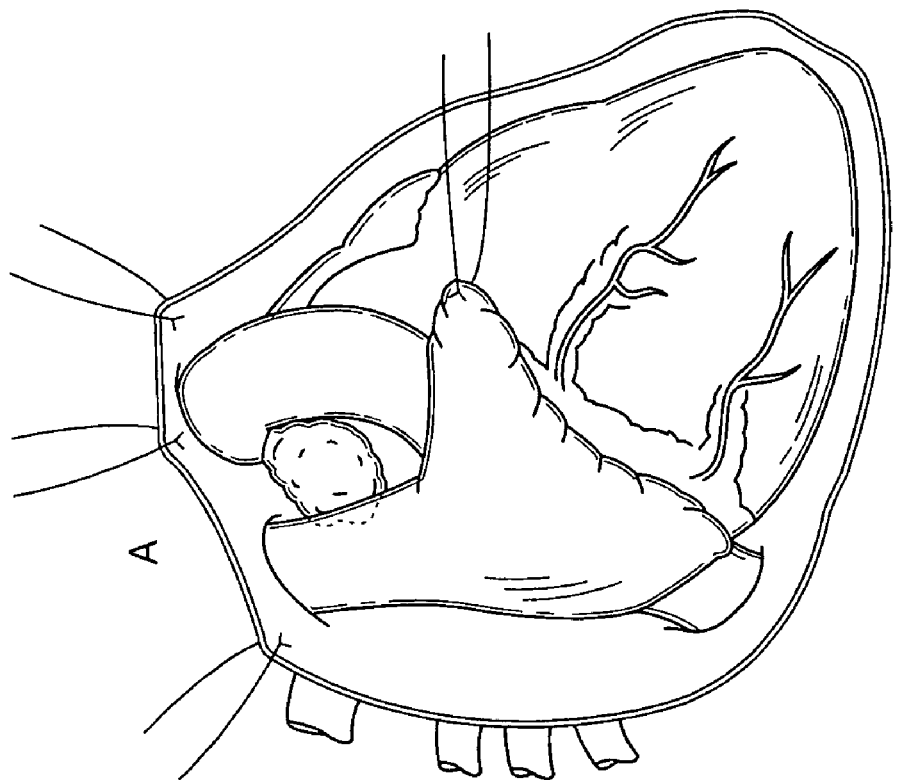

Another method of the invention includes a method of performing a 'hybrid' medical procedure comprising creating a continuous lesion encircling or partially encircling the pulmonary veins to electrically isolate the pulmonary veins during a surgical procedure and creating additional ablation lesions in the left and/or right atrium, vena cava, endocarium to the mitral valve annulus, or along the left atrial appendage to create a Maze-like lesion set for treatment of atrial fibrillation Another area that has been identified as a location for arrhythmia-triggering foci is in the parasympathetic nerves that innervate the cardiac tissue as part of the autonomic nervous system. The normal function of the cardiac parasympathetic nerves is to slow down the heart rate in a relaxation response. However, electrophysiologic changes in atrial tissues caused by parasympathetic nerve activity can result in AF. The three main ganglia of the cardiac parasympathetic nerves are located in para-cardiac fat pads, the locations of which are shown in FIGS. 11A and 11B.

1. Ganglion A, located between the superior vena cava and the aortic root just above the right superior pulmonary vein;
2. Ganglion B, located between the right superior pulmonary vein and the right atrium; and
3. Ganglion C, located between the inferior vena cava and the right/left atrium.

Ganglion B gives most of the cardiac parasympathetic innervation. Ganglion C gives origin to the main part of the AV nodal innervation. Most of the vagal efferent cardiac fibres pass through ganglion A and thence to ganglia B and C. Only a few efferent fibres directly enter the B and C ganglia. Therefore, it is feasible to achieve parasympathetic denervation by ablating ganglion B and AV nodal denervation by ablating ganglion C. However, ablation of ganglion A provides additional and significant sinus and AV node denervation.

Any of the methods and devices described above can be adapted for ablation of the cardiac parasympathetic ganglia for treating patients who are symptomatic for arrhythmia or for prophylactically treating patients determined to be at high risk for developing AF or other arrhythmias as a sequella to cardiac or thoracic surgery. The method includes steps of: verifying at least one location of a patient's cardiac parasympathetic ganglia, advancing at least one treatment member through an incision on the patient into the vicinity of the cardiac parasympathetic ganglia and applying energy to ablate at least one of the cardiac parasympathetic ganglia. The cardiac parasympathetic ganglia can be located using anatomical landmarks, using spectral mapping with Fast Fourier Transform analysis as described by Pachon et al. and/or using a pacing technique that will be described below. The ablation energy should be applied in a manner that creates superficial lesions that destroy the parasympathetic nerve cells. It is not necessary to create transmural lesions. Using the ablation devices described herein, a temperature setting of 60-65 C for a duration of 10-15 seconds, or 50 C for 30 seconds will generally destroy the parasympathetic nerve cells in the treatment area. The method can be applied in a separate procedure or it can be applied in combination with a cardiac or thoracic surgical procedure using open surgical or minimally invasive techniques. This method can also be combined with the other ablation methods described herein, particularly when multiple causes of arrhythmia are suspected.

Figure 12:
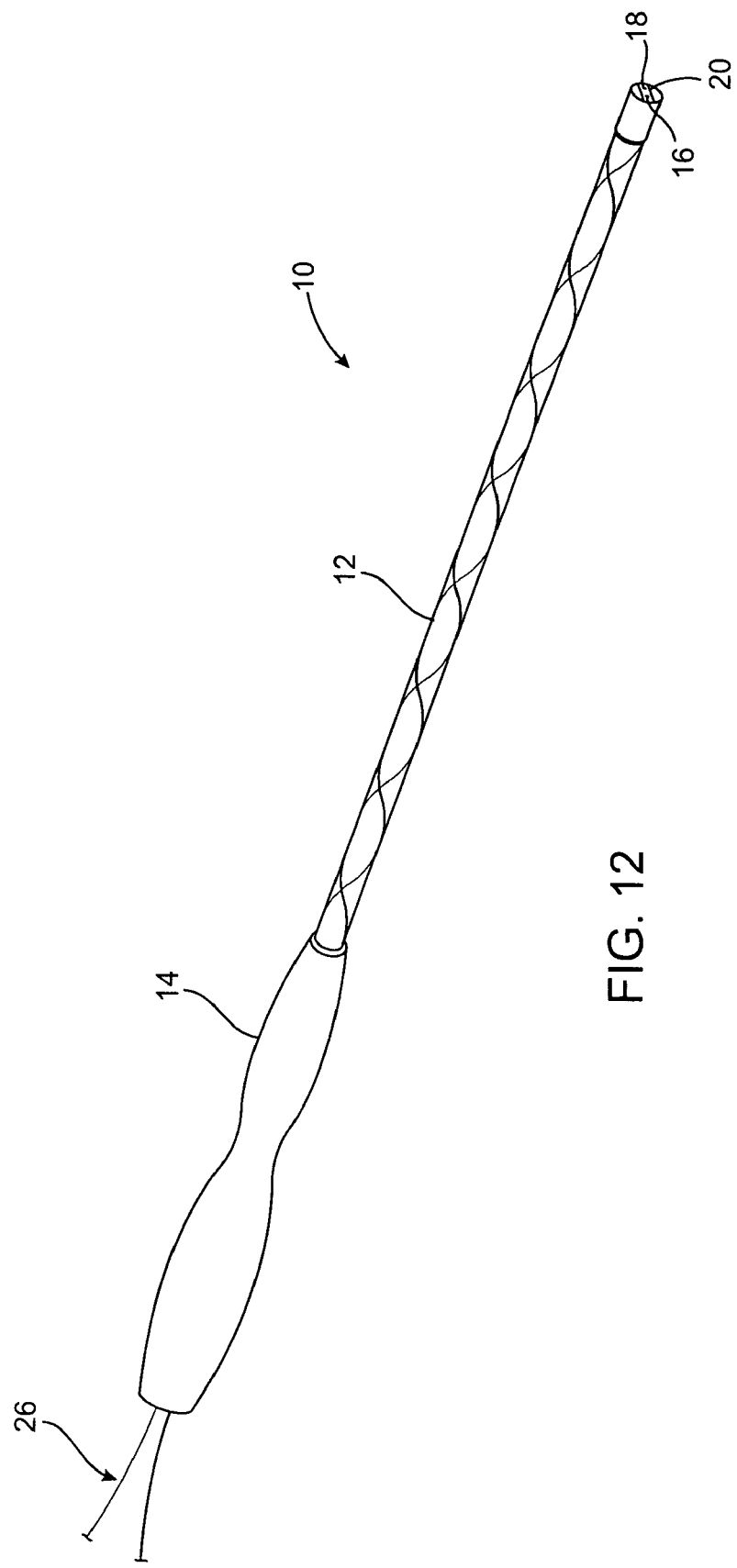
FIG. 12 shows a combined pacing and ablation probe for treating AF by ablation of the cardiac parasympathetic ganglia.
Figure 13:
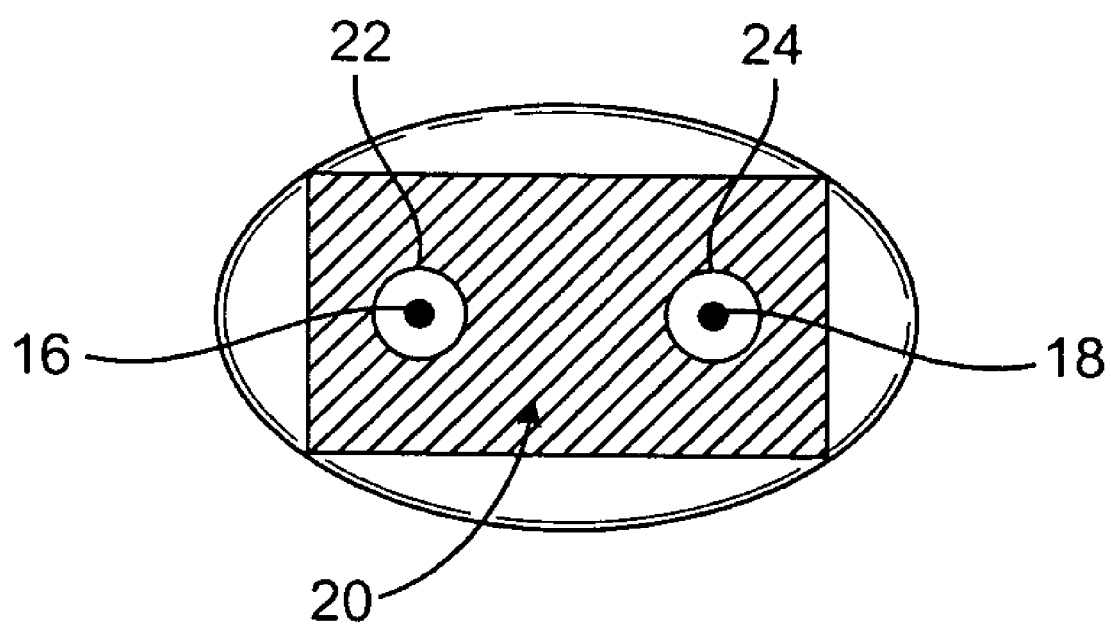
FIG. 13 shows a distal end view of the combined pacing and ablation probe of FIG. 12.
Figure 14:
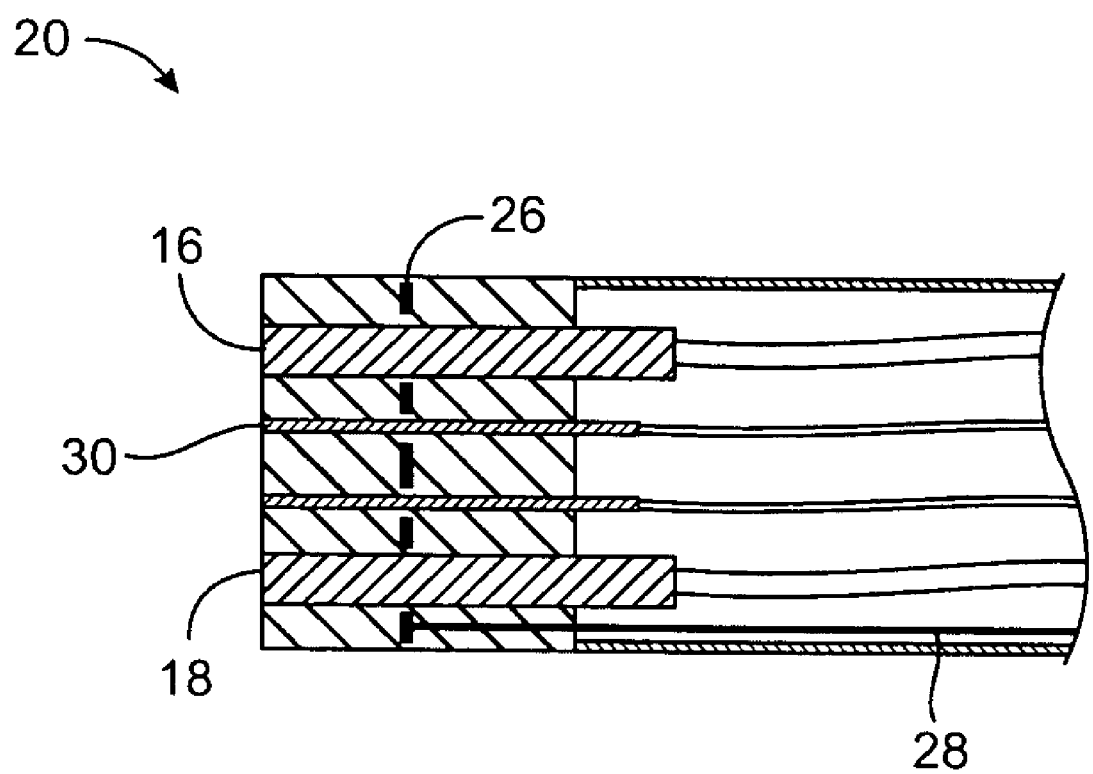
FIG. 14 shows a longitudinal cross section of the distal region of the combined pacing and ablation probe of FIG. 12.

In a particularly preferred embodiment, the method is carried out with the assistance of a combined pacing and ablation probe 10, which is shown in FIG. 12. The probe 10 is generally configured with an elongated shaft 12 connected to a handle 14. At a distal end of the elongated shaft 12, the probe 10 has a pair of pacing electrodes 16, 18 and at least one ablation electrode 20. FIG. 113 shows a distal end view and FIG. 14 shows a longitudinal cross section of the distal region of one preferred embodiment of the combined pacing and ablation probe of FIG. 12. The probe 10 has a large ablation electrode 20 with two openings 22, 24 through it. The smaller pacing electrodes 16, 18 are located in the openings 22, 24 and electrically insulated from the ablation electrode 20. The size and geometry of the electrodes is variable, but by way of example one preferred embodiment of the probe 10 will have an ablation electrode 20 in the shape of a rectangle with a width of approximately 6-7 mm and a length of approximately 15 mm. Alternatively, the ablation electrode 20 can be in the shape of an oval, circle or any other convenient shape. The pacing electrodes 16, 18 are circular with a diameter of approximately 0.5 mm. The proximal end of the probe 10 has an electrical connector adapted for connecting the probe 10 to a source of pacing signals and a source of ablation energy.

In a preferred embodiment, the ablation electrode 20 is formed of a semiconducting material, for example electrically conductive silicone rubber (loaded with graphite, for example) or a biocompatible hydrogel material, to prevent large non-uniformities in surface currents and excessive localized heating at regions of high current densities as would occur with a metallic electrode. The semiconductor ablation electrode 20 has a resistivity of 100-2000 Ω-cm. Preferably, a screen or mesh electrode 26 is used to make electrical contact between the ablation connector wire 28 and the semiconductor ablation electrode 20 to provide even distribution of the current across the face of the ablation electrode 20. The total length of the distal tip of the combined pacing and ablation probe 10 is approximately 20 mm. The wire screen is preferably within 2 mm of the end surface of the probe. Except for the distal 2 mm, the pacing electrodes 16, 18 should be insulated from the semiconducting material of the ablation electrode 20. The tips of the pacing electrodes 16, 18 may extend beyond the distal surface by up to 1.5 mm, or they can be flush with the distal surface of the ablation electrode 20.

In a preferred embodiment, a temperature sensor 30 is built into the ablation electrode 20 to monitor heating of the ablation electrode 20 and consequently the tissue in contact with it. The temperature sensor 30 can be a thermocouple or thermister type temperature sensor.

The pacing electrodes 16, 18 are used for pacing the cardiac tissue in a method to detect the location of the cardiac parasympathetic ganglia. The pacing electrodes 16, 18 are placed in contact with the epicardial or pericardial tissue using the anatomical landmarks outlined above and a pacing signal is applied through the pacing electrodes 16, 18. Preferably, the pacing signal is provided with a pacing interval of approximately 50-60 ms. (A special neurological or electrophysiology diagnostic pacer is typically needed as this is beyond the capabilities of standard cardiac pacing equipment.) When the pacing electrodes 16, 18 pass close to a parasympathetic ganglion, the ganglion is stimulated causing a relaxation response that slows the heart rate or causes the heart to stop momentarily. Once a cardiac parasympathetic ganglion has been located, RF ablation energy is applied through the ablation electrode 20 of the probe 10. The ablation energy should be applied in a manner that creates superficial lesions that destroy the parasympathetic nerve cells. It is not necessary to create transmural lesions. Ablation using a temperature setting of 60-65 C for 10-15 seconds, or 50 C for 30 seconds will generally destroy the parasympathetic nerve cells in the treatment area. The combined pacing and ablation probe 10 allows this treatment method to be applied more accurately than using a separate pacing probe and ablation electrode because the probe 10 does not have to be moved or replaced with another tool to complete the ablation procedure.

Post operative AF is a significant problem for hospitals worldwide with no effective solution. AF is the most common morbidity event after coronary bypass grafting. It has been estimated that the incidence of AF following coronary artery bypass graft (CABG) surgery is between 25% and 40%. The rate is even higher for patients undergoing valve surgery either alone or in combination with CABG surgery. The methods described herein can be applied in combination with a cardiac or thoracic surgical procedure to treat atrial fibrillation prophylactically in patients determined to be at high risk for developing atrial fibrillation as a sequella to the surgery. The methods described herein are applicable to open surgical procedures as well as less invasive of minimally invasive surgical procedures.

In a preferred method according to the invention, a minimalist approach is used for prophylactic treatment of asymptomatic patients determined to be at risk for AF. In this approach, bipolar ablation clamps or the like are used to create circular transmural lesions around each of the pulmonary veins to isolate the most common foci for the origin of arrhythmias. In combination, an ablation device, such as the combined pacing and ablation probe 10, is used to ablate one or more of the parasympathetic ganglia, as described above. For patients who are symptomatic for AF, are at high risk of developing AF or are still refractory after the minimalist treatment, a more complete maze-type ablation procedure, typically involving three lines of transmural ablation lesions, can be performed in combination with ablation of one or more of the parasympathetic ganglia to resolve and prevent recurrence of AF or other arrhythmias. The ablation method will typically be done as an adjunct to a cardiac surgical procedure, which may be performed using minimally invasive or standard open surgical techniques. Alternatively, the ablation method may be performed as a stand-alone procedure. In conjunction, other sites suspected of being the origin or conduction point of arrhythmias can be ablated. For example, the ligament of Marshall located near the left atrial appendage is known to include neural connections that may contribute to arrhythmias and can be ablated with one of the devices described herein or transected using an electrosurgical device (bovie).

While the present invention has been shown and described with reference to various embodiment thereof, the above and other changes in form and detail may be made without departing from the spirit and scope of the invention as defined in the following claims.

What is claimed is:

1. A method of treating a cardiac arrhythmia, comprising:
locating a cardiac parasympathetic ganglion by applying a pacing signal to a localized region of cardiac tissue and observing a relaxation response in the heart due to stimulation of the cardiac parasympathetic ganglion by the pacing signal; and
applying ablation energy to the cardiac parasympathetic ganglion; and
ablating a circular lesion around at least one pulmonary vein.

2. The method of treating a cardiac arrhythmia of claim 1, wherein the locating step and the ablation step are performed with a combined pacing and ablation probe.

3. The method of treating a cardiac arrhythmia of claim 2, wherein the combined pacing and ablation probe is maintained in position between the locating step and the ablation step.

4. The method of treating a cardiac arrhythmia of claim 1, wherein the relaxation response in the heart is an observed reduction in heart rate due to stimulation of the cardiac parasympathetic ganglion by the pacing signal.

5. The method of treating a cardiac arrhythmia of claim 1, wherein the pacing signal is applied at a pacing interval of approximately 50-60 ms.

6. The method of treating a cardiac arrhythmia of claim 1, further comprising performing a cardiac or thoracic surgery procedure.

7. The method of claim 1 wherein the patient is symptomatic for a cardiac arrhythmia.

8. The method of claim 6 wherein the patient is not symptomatic for a cardiac arrhythmia, but is determined to be at high risk for developing a cardiac arrhythmia as a sequella to the cardiac or thoracic surgical procedure.

9. The method of claim 1 wherein the patient is not symptomatic for a cardiac arrhythmia, but is determined to be at high risk for developing a cardiac arrhythmia due to a concomitant medical condition.

10. The method of claim 2 wherein the combined pacing and ablation probe is inserted into the patient through an incision.

11. The method of claim 1, further comprising ablating a pattern of lesions approximating the configuration of a Cox maze procedure.

12. A combined pacing and ablation probe, comprising:
an elongated shaft having a proximal end and a distal end;
a pair of pacing electrodes located at the distal end of the elongated shaft; and
an ablation electrode located at the distal end of the elongated shaft;
wherein the ablation electrode has a greater surface area than each of the pacing electrodes,
wherein the ablation electrode surrounds each of the pacing electrodes and wherein the ablation electrode is electrically insulated from each of the pacing electrodes.

13. The combined pacing and ablation probe of claim 12, wherein the pacing electrodes are electrically insulated from each other.

14. The combined pacing and ablation probe of claim 12, further comprising an electrical connector providing electrical connections to the ablation electrode and the pacing electrodes.

15. The combined pacing and ablation probe of claim 12, further comprising a handle connected to the proximal end of the elongated shaft.

16. The combined pacing and ablation probe of claim 12, further comprising a temperature sensor configured to sense the temperature of the ablation electrode.

17. A combined pacing and ablation probe, comprising:
an elongated shaft having a proximal end and a distal end;
a pair of pacing electrodes located at the distal end of the elongated shaft; and
an ablation electrode located at the distal end of the elongated shaft;
wherein the ablation electrode is made of a semiconducting material.

18. The combined pacing and ablation probe of claim 17, wherein the semiconducting material of the ablation electrode comprises graphite filled silicone.

19. The combined pacing and ablation probe of claim 17, wherein the semiconducting material of the ablation electrode comprises a hydrogel material.

20. The combined pacing and ablation probe of claim 17, wherein the ablation electrode is connected to an ablation connector wire with a mesh electrode.

21. A method of treating a cardiac arrhythmia in combination with a cardiac or thoracic surgical procedure, comprising:
performing a cardiac or thoracic surgical procedure on a patient; and
ablating heart tissue on the heart of a patient to treat a cardiac arrhythmia by contacting heart tissue with an ablation device having at least one tissue contacting member and at least one ablation member with an ablation electrode made of a semiconducting material;
positioning the tissue contacting device on the heart tissue in a position proximate at least one location selected for ablation;
applying sufficient suction force through the tissue contacting member to secure the contacting member to the tissue; positioning the ablation member within the tissue contacting device to position said ablation member adjacent to an epicardial region selected for ablating heart tissue; and applying ablation energy to at least a portion of the heart tissue with the ablation electrode.

22. The method of claim 21 wherein the patient is symptomatic for a cardiac arrhythmia.

23. The method of claim 21 wherein the patient is not symptomatic for a cardiac arrhythmia, but is determined to be at high risk for developing a cardiac arrhythmia as a sequella to the cardiac or thoracic surgical procedure.

24. The method of claim 21 wherein the patient is not symptomatic for a cardiac arrhythmia, but is determined to be at high risk for developing a cardiac arrhythmia due to a concomitant medical condition.

25. The method of claim 21 wherein the ablation device is inserted into the patient through an incision.

26. The method of claim 21, further comprising:
applying a pacing signal to the heart with a pair of pacing electrodes located on the ablation device.

27. The method of claim 26, further comprising:
locating a cardiac parasympathetic ganglion by applying the pacing signal to a localized region of cardiac tissue and observing a relaxation response in the heart due to stimulation of the cardiac parasympathetic ganglion by the pacing signal; and applying the ablation energy to the cardiac parasympathetic ganglion.

28. The method of claim 27, wherein the pacing signal is applied at a pacing interval of approximately 50-60 ms.

\* \* \* \* \*